United States Patent
Karanassios

(10) Patent No.: US 7,460,225 B2
(45) Date of Patent: Dec. 2, 2008

(54) MINIATURIZED SOURCE DEVICES FOR OPTICAL AND MASS SPECTROMETRY

(76) Inventor: Vassili Karanassios, 235 Erb Street West, Apartment 508, Waterloo, Ontario (CA) N2L 1V9

( * ) Notice: Subject to any disclaimer, the term of this patent is extended or adjusted under 35 U.S.C. 154(b) by 207 days.

(21) Appl. No.: 11/072,330

(22) Filed: Mar. 7, 2005

(65) Prior Publication Data

US 2005/0195393 A1 Sep. 8, 2005

Related U.S. Application Data

(60) Provisional application No. 60/550,052, filed on Mar. 5, 2004.

(51) Int. Cl.
*G01J 3/30* (2006.01)
*G01N 1/10* (2006.01)

(52) U.S. Cl. .................. 356/316; 356/246

(58) Field of Classification Search .......... 356/316, 356/246, 36, 44, 49, 50, 311
See application file for complete search history.

(56) References Cited

U.S. PATENT DOCUMENTS

| | | | | |
|---|---|---|---|---|
| 3,591,289 | A * | 7/1971 | Donega et al. | 356/312 |
| 4,330,208 | A * | 5/1982 | Eloy | 356/318 |
| 5,256,374 | A * | 10/1993 | De Silva et al. | 422/80 |
| 5,705,787 | A * | 1/1998 | Karanassios | 219/121.52 |
| 5,896,196 | A * | 4/1999 | Pinnaduwage | 356/316 |
| 5,942,855 | A | 8/1999 | Hopwood | |
| 6,184,982 | B1 | 2/2001 | Karanassios | |
| 6,381,014 | B1 | 4/2002 | Platzer et al. | |
| 6,392,188 | B1 * | 5/2002 | Milani et al. | 219/121.43 |
| 6,686,998 | B2 * | 2/2004 | Gianchandani et al. | 356/316 |
| 6,734,964 | B1 * | 5/2004 | Duan et al. | 356/316 |
| 6,759,808 | B2 | 7/2004 | Grotjohn et al. | |
| 7,081,623 | B2 * | 7/2006 | Pai et al. | 250/299 |
| 7,123,361 | B1 * | 10/2006 | Doughty | 356/316 |
| 2003/0070913 | A1 * | 4/2003 | Miller et al. | 204/192.1 |
| 2005/0121607 | A1 * | 6/2005 | Miller et al. | 250/287 |
| 2005/0211910 | A1 * | 9/2005 | Bloom et al. | 250/423 P |

(Continued)

FOREIGN PATENT DOCUMENTS

WO WO 98/36440 8/1998

OTHER PUBLICATIONS

Feynman, R. P., "There's Plenty of Room at the Bottom" transcript of talk from Dec. 29, 1959 at the annual meeting of the American Physical Society at the California Institute of Technology, Full text at, http://www.zyvek.com/nanotech/feynman.html (accessed Nov. 3, 2003).

(Continued)

*Primary Examiner*—Patrick Connolly
*Assistant Examiner*—Scott M Richey
(74) *Attorney, Agent, or Firm*—Bereskin & Parr

(57) ABSTRACT

Low-power, low flow-rate, portable, miniaturized plasma devices are provided. A portable, low-power, low flow-rate, miniaturized sample introduction device is also provided. The devices are inexpensive to make, have low operating cost and can be used with a variety of gases and gas mixtures. The devices can be used for elemental analysis from liquid or solid micro-samples by optical emission or mass spectrometry provided that an appropriate sample introduction system is used.

15 Claims, 19 Drawing Sheets

U.S. PATENT DOCUMENTS

2006/0286492 A1* 12/2006 Morrisroe ..................... 431/2
2007/0108910 A1* 5/2007 Eden et al. .................. 313/631

OTHER PUBLICATIONS

Drexler, K. Eric "Nanosystems: Molecular Machinery, Manufacturing, and Computation", Wiley Interscience (1992). Updates can be found on the web at, http://www.foresight.org/Updates/Update15/Update 15.6.html#anchor486157 (accessed, Nov. 23, 2003) and, a special issue, "Nanoelectronics and nanoscale processing" Proceedings of the IEEE November (2003).
A journal entitled "Lab on a Chip" published by the Royal Society for Chemistry, http://www.rsc.org/is/journals/current/loc/locpub.htm.
Blades, M. W. and Karcus, R. K. (organizers), "Miniaturization in Analytical Atomic Spectrometry: we're behind the curve", Pittsburgh conference, New Orleans, Mar. 2002.
Karanassios, V., "Plasmas on a chip: Microplasma devices", Winter Conference on Plasma Spectrochemistry, Scottsdale, AZ, USA, Jan. 9 (2002).
Karanassios, V., (organizer), "Miniaturization and microplasmas", Symposium title, FACSS conference, Providence, Rhode Island, USA, Oct. 17 (2002).
"New instrumentation and alternative plasma sources" session held at the European Winter Conference on Plasma Spectrochemistry, Garmish-Pertenkirchen, germany, Jan. 15, (2003).
Karanassios, V., "Plasmas on-a-chip", ICP Inf. Newslett., 27(10), 713-717 (2002).
A. Bass, C. Chevalier and M. W. Blades, "A capacitively coupled microplasma (CCµP) formed in a channel in a quartz wafer", J. Anal. Atom. Spectrom., 16, 919-921 (2001).
C. Brede, S. Pedersen-Bjergaard, E. Lundanes and T. Greibrokk, "Microplasma Mass Spectrometric Detection in Capillary Gas Chromatography", Anal. Chem., 70, 513-518 (1998).
C. Brede, E. Lundanes, T. Greibrokk and S. Pedersen-Bjergaard, "Capillary Gas Chromatography Coupled with Microplasma Mass Spectrometry—Improved Ion Source Design Compatible with Bench-Top Mass Spectrometric Instrumentation", J. High Resol. Chromatogr., 21, 282-286 (1998).
C. Brede, E. Lundanes, T. Greibrokk and S. Pedersen-Bjergaard, "Stimultaneous Element-Selective Detection of C, F, Cl, Br and I by Capillary Gas Chromatography Coupled with Microplasma Mass Spectrometry", J. High. Resol. Chromatogr., 21, 633-639 (1998).
C. Brede, S. Pedersen-Bjergaard, E. Lundanes and T. Greibrokk, "Capillary gas chromatography coupled with microplasma mass spectrometry for organotin speciation", J. Chromatogr. A, 849, 553-562 (1999).
T. Greibrokk, C. Brede, S. Pedersen, S. Perdersen-Bjergaard and E. Lundanes, "Simultaneous element-selective detection of halogenated compounds", Am. Lab., 31, 24-30 (Jun. 1999).
C. Brede, S. Pedersen-Bjergaard, E. Lundanes and T. Greibrokk, "Capillary gas chromatography coupled with negative ionization microplasma mass spectrometry for halogen-selective detection", J. Anal. Atom. Spectrom., 15, 55-60 (2000).
A. M. Bilgic, U. Engel, E. Voges, M. Kuckelheim and J. A. C. Broekaert, "A new low-power microwave plasma source using microstrip technology for atomic emission spectrometry", Plasma Sources Sci. Technol., 9, 1-4 (2000).
U. Engel, A. M. Bilgic, O. Haase, E. Voges and J. A. C. Broekaert, "A Microwave-Induced Plasma Based on Microstrip Technology and Its Use for the Atomic Emission Spectrometric Determination of Mercury with the Aid of the Cold-Vapor Technique", Anal. Chem., 72, 193-197 (2000).
A. M. Bilgic, E. Voges, U. Engel and J. A. C. Broekaert, "A low-power 2.45 GHz microwave induced helium plasma source at atmospheric pressure based on microstrip technology", J. Anal. Atom. Spectrom., 15, 579-580 (2000).
J. A. C. Broekaert, "The development of microplasmas for spectrochemcial analysis", Anal. Bional. Chem., 374, 182-187 (2002).
S. Schermer, N. H. Bings, A. M. Bilgic, R. Stonies, E. Voges and J. A. C. Broekaert, "An improved microstrip plasma for optical emission spectrometry of gaseous species", Spectrochim. Acta, 58B, 1585-1596 (2003).
C. G. Wilson and Y. B. Gainchandani, "Spectral Detection of Metal Contaminants in Water Using an On-Chip Microglow Discharge", IEEE Trans. Electr. Dev., 49, 2317-2322 (2002).
R. Guchardi and P. C. Hauser, "A capacitively coupled microplasma in a fused silica capillary", J. Anal. Atom. Spectrom., 18, 1056-1059 (2003).
Y. Yin, J. Messier and J. A. Hopwood, "Miniaturization of Inductively Coupled Plasma Sources", IEEE Trans. Plasma Science, 27, 1516-1524 (1999).
J. A. Hopwood, "A Microfabricated Inductively Coupled Plasma Generator", J. Micro Electro Mechanical Systems, 9, 309-313 (2000).
J. Hopwood, O. Minayeva and Y. Yin, "Fabrication and characterization of a micromachined 5 mm inductively coupled plasma generator", J. Vac. Sci. Techno!. B, 18, 2446-2451 (2000).
F. Iza and J. Hopwood, "Influence of operating frquency and coupling coefficient on the efficiency of microfabricated inductively coupled plasma sources", Plasma Sources Sci. Tech., 11, 229-235 (2002).
O. B. Minayeva and J. A. Hopwood, "Emission spectroscopy using a microfabricated inductively coupled plasma-on-a-chip", J. Anal. Atom. Spectrom., 17, 1103-1107 (2002).
J. A. Hopwood, "Micromachined inductively coupled plasma generators: Applications and scaling laws", pp. 63-67, Proceedings of International Symposium on Dry Process (DPS2002), Oct. 10-11, Tokyo, Japan (2002).
O. B. Minayeva and J. A. Hopwood, "Microfabricated inductively coupled plasma-on-a-chip for molecular $SO_2$ detection: a comparison between global model and optical emission spectrometry", J. Anal. Atom. Spectrom., 18, 856-863 (2003).
O. B. Minayeva and J. Hopwood, "Langmuir probe diagnostics of a microfabricated inductively coupled plasma on a chip"J. Appl. Phys., 94, 2821-2828 (2003).
F. Iza and J. A. Hopwood, "Low-Power Microwave Plasma Source Based on a Microstrip Split-Ring Resonator", IEEE Trans. Plasma Science, 31, 782-787 (2003).
T. Ichiki, T. Koidesawa and Y. Horiike, "An atmosphere-pressure microplasma jet source for the optical emission spectroscopic analysis of liquid sample", Plasma Source Sci. Technol., 12, S16-S20 (2003).
K. Johnson, W. Vander Wilp and V. Karanassios, "Micro-fluidics in Environmental Monitoring: Liquid Micro-samples by an In-Torch Vaporization—Micro-Plasma Device (ITV-MPD)", first presented at the SPIE conference in Boston in Oct. 2000 and published in SPIE Proceedings, 4205,347-352 (2001).
V. Karanassios, "Taking (part of) the Lab to the Sample: From Nano-samples to Micro-Plasmas on a Chip", Porc., Fourth Biennial International Conference on Monitoring and Measurement of the Environment, R. Clement and B. Burk (Eds.), 4, 339-404 (2002).
V. Karanassios, "Discrete sample introduction system for a battery-operated micro plasma device (MPD) on-a-chip", Paper 633, Federation of Analytical Chemistry and Spectroscopy Societies (FACSS) conference, Rhode Island, Providence, USA (Oct. 13-17, 2002).
V. Karanassios, "Plasmas-on-a-chip", short course, most recently offered at the 49th International Conference on Analytical Sciences and Spectroscopy (ICASS), Ottawa, Ontario, Canada, Jun. 1 (2003).
J. C. T. Eijkel, H. Stoeri and A. Manz, "A Molecular Emission Decector on a Chip Employing a Direct Current Microplasma", Anal. Chem., 71, 2600-2606 (1999).
J. C. T. Eijkel, H. Stoeri and A. Manz, "A dc Microplasma on a Chip Employed as an Opitcal Emission Detector for Gas Chromatography", Anal. Chem., 72, 2547-2552 (2000).
J. C. T. Eijkel, H. Stoeri and A. Manz, "An atmospheric pressure dc glow discharge on a microchip and its application as a molecular emission detector", J. Anal. Atom. Spectrom., 15, 297-300 (2000).
F. G. Bessoth, O. P. Naji, J. C. T. Eijkel and A. Manz, "Towards an on-chip gas chromatograph: the development of a gas injector and a dc plasma emission detector", J. Anal. Atom. Spectrom., 17, 794-799 (2002).

G. Jenkins and A. Manz, "A miniaturized glow discharge applied for optical emission detection in aqueous analytes", J. Micromechanics and Microengineering, 12, N19-N22 (2002).

W. C. Davis and R. K. Marcus, "An atmospheric pressure glow discharge optical emission source for the direct sampling of liquid media", J. Anal. Atom. Spectrom., 16, 931-937 (2001).

R. K. Marcus and W. C. Davis, "An Atomspheric Pressure Glow Discharge Optical Emission Source for the Direct Sampling of Liquid Media", Anal. Chem., 73, 2903-2910 (2001).

W. C. Davis and R. K. Marcus, "Role of powering geometrics and sheath gas composition on operation characteristics and the optical emission in the liquid sampling-atmospheric pressure glow discharge", Spectrochim. Acta, 57B, 1473-1486 (2002).

W. C. Davies, D. Strand and R. K. Marcus, "Elemental speciation: Separation and detection of metal cations using a low-power atmospheric pressure plasma", Am. Lab., 28-29, Apr. (2003).

M. Miclea, K. Kunze, G. Musa, J. Franzke and K. Niemax, "The dielectric barrier discharge—a powerful microchip plasma for diode laser spectrometry", Spectrochim. Acta, 56B, 37-43 (2001).

K. Kunze, M. Miclea, G. Musa, J. Franzke, C. Vadla and K. Niemax, "Diode laser-aided diagnostics of a low-pressure dielectric barrier discharge applied in element-selective detection of molecular species", Spectrochim. Acta, 57B, 137-146 (2002).

M. Miclea, K. Kunze, J. Franzke and K. Niemax, "Plasma for lab-on-the-chip applications", Spectrochim. Acta, 57B, 1585-1592 (2002).

C. Penache, M. Miclea, A. Brauning-Demain, O. Hohn, S. Schossler, T. Jahnke, K. Neimax and H. Schmidt-Bocking, "Characterization of a high-pressure microdischarge using diode laser atomic absorption spectroscopy", Plasma Sources Sci. Technol., 11, 476-483 (2002).

K. Kunze, M. Miclea, J. Franzke and K. Niemax, "The dielectric barrier discharge as a detector for gas chromatography", Spectrochim. Acta, 58B, 1435-1443 (2003).

J. Franzke, K. Kunze, M. Milcea and K. Niemax, "Microplasmas for analytical spectrometry", J. Anal. Atom. Spectrom., 18, 802-807 (2003).

K. Cziesla, B. Platzer, M. Okruss, S. Florek and M. Otto, "Hyphenation of a near-infrared Echelle spectrometer to a microplasma for element-selective detection in gas chromatography", Frez. J. Anal. Chem., 371, 1043-1046 (2001).

X. Quan, S. Chen, B. Platzer, J. Chen and M. Gfrerer, "Simultaneous determination of chlorinated organic compounds from enviromental samples using gas chromatography coupled with a micro electron capture detector and micro-plasma atomic emission detector", Spectrochim. Acta, 57B, 189-199 (2002).

V. Siemens, "A new microstrip size radio frequency plasma in optical emission spectrometry", Paper 638, Federation of Analytical Chemistry and Spectroscopy Societies (F ACSS) conference, Providence, Rhode Island (Oct. 2002).

H. Yoshiki and Y. Horiike, "Capacitively Coupled Microplasma Source on a Clip at Atmospheric Pressure", Jpn. J. Appl. Phys., 40, L360-L362 (2001).

H. Yoshiki, A. Oki, H. Ogawa and Y. Horiike, "Inner wall modification of a poly(ethylene terephthalate) (PET) capillary by 13.56 MHz capacitively coupled microplasma", Thin Solid Films, 407, 156-162 (2002).

K. Taniguchi, T. Fukasawa, H. Yoshiki and Y. Horiike, "Generation of Integrated Atmospheric Microplasmas", pp. 75-80, Proceedings of International Symposium on Dry Process (DPS2002), Oct. 10-11, Tokyo, Japan (2002).

P.-A. Auroux, D. Iossifidis, D. R. Reyes and A. Manz, "Micro Total Analysis System 2. Analytical Standard Operations and Applications", Anal. Chem., 74, 2637-2652 (2002).

A. Wijaya, S. Zuo, T. A. Grotjohn and J. Asmussen, "Miniature microwave plasma sources based on microstripline designs", Paper 6A06, 29th IEEE conference on plasma science (ICOPS2002), Banff, Alberta, May 26-30, 2002.

U. Kogelschatz, B. Eliasson and W. Egli, "From ozone generators to flat television screens: history and future potential of dielectric-barrier discharges", IUPAC Pure Appl. Chem., 71, 1819-1828 (1999).

K. Okazaki and T. Nozaki, "Ultrashort pulsed barrier discharges and applications", IUPAC Pure Appl. Chem., 74, 447-452 (2002).

L. Baars-Hibbe, P. Sichler, C. Schrader, C. Gebner, K-H. Gericke and S. Buttgenbach, "Micro-structured electrode arrays: Atmospheric pressure plasma processes and applications", Surface Coatings and Technology, 174-175 (2003) 519-523.

R. H. Stark and K. H. Schoenbach, "Direct current high-pressure glow discharges", J. Appl. Phys., 85, 2075-2080 (1999).

A.-A. H. Mohamed, R. Block and K. H. Schoenbach, "Direct Current Glow Discharges in Atmospheric Air", IEEE Trans. Plasma Sci., 30, 182-183 (2002).

M. Moselhy, I. Petzenhauser, K. Frank and K. H. Schoenbach, "Excimer emission from microhollow cathode argon discharges", J. of Phys. D: Appl. Phys., 2922-2927 (2003).

S-J. Park, J. Chen, C. J. Wagner, N. P. Ostrom, C. Liu and J. G. Eden, "Microdischarge Arrays: A New Family of Photonic Devices (Revised)", IEEE J. Select. Topics Quantum Electron., 8, 387-394 (2002).

Y-B. Guo and F. Chau-Nan Hong, "Radio-frequency microdischarge arrays for large-area cold atmospheric plasma generation", Appl. Phys. Lett., 82, 337-339 (2003).

The 3rd international workshop on Basic Aspects of Non-equilibrium Plasmas Interacting with Surfaces (BANPIS'03) was devoted to the "physics and applications if microplasmas". A special issue on papers from BANPIS'03 has been published in the Journal of Applied Physics D: Applied Physics.

J. G. Eden, S-J. Park, N. P. Ostrom, S. T. McCain, C. J. Wagner, B. A. Vojak, J. Chen, C. Liu, P. Von Allmen, F. Zenhausern, D. J. Sadler, C. Jensen, D. L. Wilcox and J. J. Ewing, "Microplasma devices fabricated in silicon, ceramic, and metal/polymer structures: arrays, emitters, and photodetectors", J. of Phys. D: Appl. Phys., 36, 2869-2877 (2003).

D. D. Hsu and D. B. Graves, "Microhollow cathode discharge stability with flow and reaction", J. Phys. D: Appl. Phys., 36, 2898-2907 (2003).

R. M. Sankaran and K. P. Giapis, "High-pressure micro-discharges in etching and deposition applications", J. of Phys. D: Appl. Phys., 36, 2914-2921 (2003).

T. Cserfalvi, P. Mezei and P. Apai, "Emission studies on a glow discharge in atmospheric pressure air using water as a cathode", J. Phys. D: Appl. Phys., 26, 2184-2188 (1993).

H. J. Kim, J. H. Lee, M. Y. Kim, T. Cserfalvi and P. Mezei, "Development of open-air type electrolyte-as-cathode glow discharge-atomic emission spectrometry for determination of trace metals in water", Spectrochim. Acta, 55B, 823-831 (2000).

S. Pedersen-Bjergaard and T. Greibrokk, "On-Column Bromine- and Chlorine-Selective Detection for Capillary Gas Chromatography Using a Radio Frequency Plasma" Anal. Chem., 65, 1998-2002 (1993).

M. Kuzuya and E. H. Piepmeier, "Oscillating-Plasma Glow Discharge as a Detector for Gas Chromatography", Anal. Chem., 63, 1763-1766 (1991).

S. A. Estes, P. C. Uden and R. M. Barnes, "Microwave-Excited Atmospheric Pressure Helium Plasma Emission Detection Characteristics in Fused Silica Capillary Gas Chromatography", Anal. Chem., 53, 1829-1837 (1981).

H. Ogino and T. Seki, "Development of a Detector for Ultratrace Nitrogen in Argon Using Low-Pressure, Capillary Glow Discharge Molecular Emission Spectrophotometry", Anal. Chem., 69, 3636-3640 (1997).

B. D. Quimby and J. J. Sullivan, "Evaluation of a Microwave Cavity, Discharge Tube, and Gas Flow System for Combined Gas Chromatography-Atomic Emission Detection", Anal. Chem., 62, 1027-1034 (1990).

J. W. Olesik, "Investigating the Fate of Individual Sample Droplets in Inductively Coupled Plasmas", Appl. Spectrosc., 51, 158A-175A (1997).

V. Karanassios, V. Grishko and G. G. Reynolds, "Elemental analysis of micro-samples of liquids or slurries by coiled-filament in-torch vaporization-inductively coupled plasma atomic emission spectrometry (ITV-ICP-AES)", J. Anal. Atom. Spectrom., 14, 565-570 (1999).

V. Karanassios and G. Mew, "Anisotropic Wet Chemical Etching of Si for Chemical Analysis Applications", Sensors and Materials, 9, 395-416 (1997).

D. Beauchemin, D. C. Gregoire, D. Gunther, V. Karanassios, J.-M. Mermet and T. J. Wood, "Discrete Sample Introduction Techniques For Inductiely Coupled Plasma Mass Spectrometry", 596 pages, Elsevier, Netherlands (2000).

H. R. Badiei, A. T. Smith and V. Karanassios, "Rhenium-cup, in torch vaporization (ITV) sample introduction for axially viewed ICP-AES and its application to the analysis of a microscopic, ng-weight solid sample", J. Anal. Atom. Spectrom., 17, 1030-1036 (2002).

H. R. Badiei, M. A. Rutzke and V. Karanassios, "Calcium content of individual, microscopic, (sub) nanoliter volume *Paramecium sp.* cells using rhenium-cup in-torch vaporization (ITV) sample introduction and axially viewed ICP-AES", J. Anal. Atom. Spectrom., 17, 1007-1010 (2002).

R. McCulloch and V. Karanassios, "Portability for *On-site* Environmental Monitoring: Parameters Affecting Resolution of Small-size and Miniature Optical Spectrometers", Proc., Fourth Biennial Intern. Conf. on Mon. and Meas. of the Env. (EnviroAnalysis), R. Clement and B. Burk (Eds.), 4, 215-220 (2002).

A. T. Smith and V. Karanassios, "Portability for *On-site* Environmental Monitoring: The State-of-the-art in Miniature Mass Spectrometers", Proc., Fourth Biennial Intern. Conf. on Mon. Meas. of the Env. (EnviroAnalysis), R. Clement and B. Burk (Eds.), 4, 303-308 (2002).

A. Kolkiewicz and V. Karanassios, "Transient Signal Processing Software for Analytical Determinations in the Field using a Palm-size computer", Proc., Fourth Biennial Intern. Conf. on Mon. and Meas. of the Env. (EnviroAnalysis), R. Clement and B. Burk (Eds.), 4, 227-232 (2002).

V. Karanassios, "Paradigm Shift in Classical Elemental Analysis", Spectrosc. Spect. Anal., 23, 104-114 (2003).

Special issue, Journal of Analytical Atomic Spectrometry, Jan. (2000).

V. Karanassios, "Imagineering the Future of Chemical Instumentation", Plenary lecture, 47th International Conference on Analytical Sciences and Spectroscopy, Toronto, (Aug. 20, 2001).

Symposium organized by V. Karanassios entitled "Microplasmas: The Next Frontier of Plasma Spectrochemistry" to be held at the Pittsburgh conference, Mar. 7-12 (2004).

V. Karanassios & J. T. Sharples, "Microchannels and Microcells for Gaseous Microsamples", Sensors and Materials 9, pp. 363-378, 1997.

V. Karanassios, "Microplasmas for chemical analysis: analytical tools or research toys?", Spectrochimica Acta, Part B 59 (2004) 909-928.

V. Karanassios, "Development and characterization of battery-operated micro plasma devices (MPDs)", European Conference on Plasma Spectrochemistry, Budapest, Hungary, Jan. 30-Feb. 3, 2005.

V. Siemens, Paper 019, "Characterization of a microchip size radio frequency plasma in optical emission spectrochemistry", European Winter Conference on Plasma Spectrochemistry, Garmish-Patenkirchen, Germany, Jan. 12-17 (2003).

* cited by examiner

MINIATURIZED SOURCE DEVICES FOR OPTICAL AND MASS SPECTROMETRY

CROSS REFERENCE

This application claims priority from U.S. Provisional Application Ser. No. 60/550,052 filed on Mar. 5, 2004.

FIELD OF THE INVENTION

The invention relates to miniature and micro plasma devices suitable for chemical analysis either in a laboratory or in the field.

BACKGROUND OF THE INVENTION

Plasma sources are extensively used to generate photons or ions from sample analytes. In elemental analysis in particular, plasmas are extensively used as analytical tools for environmental monitoring. Due to health concerns, there is a need to improve the capability to monitor the environment. This involves analyzing a larger number of samples which typically occurs in the lab. However, in many cases, such as when accidental spills occur for example, improvements in monitoring the environment can be achieved by obtaining analytical results on-site (i.e. in the field) and in (near) real-time. However, analytical equipment cannot be taken out of the lab for use in the field. Furthermore, analysis of a large number of samples is prohibitive due to the costs involved. In such cases, a large number of samples can only be analyzed if the cost per analysis is reduced, for instance, by reducing the operating cost of the analysis equipment.

Analysis equipment that employs plasma spectrochemistry is useful for environmental monitoring. There are several different types of plasma sources that can be used with this equipment such as inductively or capacitively coupled plasmas, radio frequency or microwave induced plasmas, glow discharges or dielectric barrier discharges, etc. However, with this type of analytical equipment, the plasma source is typically tethered to a wall socket due to the high electrical power requirements of the equipment. Further, the analysis equipment is firmly installed in the lab due its weight, size and gas consumption.

For example, an Inductively Coupled Plasma (ICP) source with a water-cooled load coil is the most widely used plasma source for elemental and isotopic analysis. A pneumatic nebulizer is generally used for introducing liquid samples into the ICP source. For elemental or isotopic analysis, the ICP source requires 1-2 kW of power, and the customarily used ICP torch requires an aggregate gas flow-rate of 12-20 L/min. Due to the relatively large flow-rate and its associated cost, the typical ICP source uses Ar gas which is delivered from bulky and heavy containers, such as compressed-gas cylinders. Additionally, for optimum operation, the pneumatic nebulizer operates continuously using approximately 1-4 mL/min of sample and requiring a carrier-gas with a flow-rate of about 0.7-1.2 L/min. Furthermore, since a nebulizer can only be used with liquids, solids must first be converted to a liquid (e.g. digested using strong acids) prior to their introduction into an ICP source. Because many analytical samples naturally occur as solids, and since acid digestion in the field is unlikely (due in part to safety concerns), use of a nebulizer for sample introduction into portable plasma sources that can be used in the field is unlikely. Furthermore, because there are numerous applications in which very little sample is available for analysis, the requirement for a sample volume on the order of milliliters further restricts nebulizer applicability. This is of particular importance in limited sample-size applications. Additionally, pneumatic nebulizers have low sample introduction efficiency (~1%), thus degrading detection limits.

Accordingly, there is a need for analysis equipment that has low power and low gas consumption for reducing cost per analysis. Further, there is a need for analysis equipment that is portable so that it can be used in the field. However, for plasma sources to be useful in environmental analysis, there must be a means for introducing analytical samples into them. Accordingly, there is also a need for analysis equipment with an interface or introduction component that can be used to introduce the analytes into the plasma source. One possible solution includes using a miniaturized plasma source with an appropriate interface. The term "miniaturized plasma" will be used in the following discussion as a means of illustration rather than limitation.

Plasma miniaturization is receiving increased attention in the current literature. However, some of the conventional microplasma sources require as much as 200 Watts of electrical power while others require vacuum pumps for proper operation, thus clearly preventing portability. As well, the recent work on conventional microplasma sources do not focus on sample introduction. In fact, most conventional microplasma sources typically simply use gaseous samples because such samples are relatively easy to introduce into microplasma sources. Others required use of high concentrations of a supporting electrolyte (e.g., 0.5 M $HNO_3$ needed to make the pH approximately 1, thus possibly giving rise to contamination and making waste disposal an issue). In addition, they either required a pump to deliver mL/min volumes of sample (thus needing a pump for proper operation) or they required relatively high electrical power levels (e.g., 50-150 Watts) to vaporize the water solvent. Both of these clearly disable portability. In one instance, use of μL volumes of sample and low power (e.g., in the Watts range) operation has been reported. But, there were difficulties with liquid sample introduction and poor sensitivities (in the 10,000 ppm range) were reported. As well as, the device could not be used with gaseous or solid samples. Overall, no microplasma sources have been developed that can be used with all three sample types: namely liquids, solids or gases. Accordingly, conventional microplasma sources restrict analytical capability, utility and applicability by excluding the majority of analytical samples that naturally occur as liquids or solids. For these conventional microplasma sources, it is not clear whether the type of interface used for sample introduction results in the predominant use of gaseous samples.

SUMMARY OF THE INVENTION

The invention provides a low power consumption (<10 Watts), preferably battery-operated, low-flow rate (e.g., 10-350 mL/min), self-igniting, atmospheric pressure, portable, miniaturized plasma source device suitable for chemical analysis either in a laboratory or the field. The miniaturized plasma source device preferably has at least one dimension in the millimeter range. The invention also includes a micro plasma source device that preferably has at least one dimension in the micrometer or smaller range. For ease of description, the miniature and micro plasma source devices will be collectively referred to as miniaturized plasma source devices. The miniaturized plasma source devices may have one of a planar or tubular geometry, for example, and are inexpensive to make and to operate.

The invention further provides miniaturized, light-weight, low flow-rate, battery-operated sample introduction devices that are capable of delivering liquid or solid micro or nano-size samples into the miniaturized plasma source devices. In one instance, the sample introduction interface may be a miniaturized ITV sample introduction device.

A unique aspect of the invention is that the miniaturized devices are well matched to each other and that analytical measurements can be made using optical (e.g. emission, absorption, fluorescence) or mass spectrometric measurements. The size and weight of both devices (excluding gas cylinder, batteries or other power supplies) is much less than that of a hand-held calculator.

These miniaturized devices and interfaces are well-suited for environmental monitoring and provide other advantages. For instance, a miniaturized plasma source reduces power and gas consumption, thus also reducing operating cost. Furthermore, miniaturized plasma sources, especially if they are micro-fabricated, can be mass-produced thus also reducing manufacturing and purchasing costs. In addition to cost savings, the miniaturized devices can be embedded into other portable instruments, such as gas chromatography devices, to serve as detectors.

Accordingly, in one aspect, at least one embodiment of the invention provides a miniaturized plasma device for generating one of sample analyte ions or sample analyte photons from a sample analyte. The miniaturized plasma device includes a microplasma chamber for receiving the sample analyte; first and second opposing electrodes disposed on opposite sides of the microplasma chamber; and, a power supply connected to the first and second opposing electrodes. In use, the power supply applies a voltage to the first and second opposing electrodes for generating the one of the sample analyte ions or sample analyte photons from the sample analyte.

The miniaturized plasma device may further include first and second opposed wafers; microchannels located on the surface of at least one of the wafers for forming an inlet conduit, an outlet conduit and the microplasma chamber with the inlet conduit and outlet conduit being disposed on either side of the microplasma chamber at an angle thereto; and, entrance and exit tubes connected to the inlet and outlet conduits respectively.

The electrodes may be disposed substantially coplanar with the microplasma chamber and the electrodes include a large portion for connection to the power supply and an inwardly disposed smaller portion being substantially collinear with the microplasma chamber.

Alternatively, the miniaturized plasma device may further include first and second opposed wafers; and, first and second opposed side walls disposed between the first and second wafers, the microplasma chamber being formed between the first and second wafers and the first and second opposed side walls with a first end portion of the microplasma chamber serving as an inlet conduit and a second end portion of the microplasma chamber serving as an outlet conduit, wherein, the electrodes are disposed on opposing facing surfaces of the first and second wafers, and each electrode includes a longitudinally extending portion for connection to the power supply and an inwardly transversely disposed portion wherein the inwardly disposed transverse portions of the electrodes substantially overlap one another in the region of the microplasma chamber.

In another alternative, the miniaturized plasma device may further include a tube for forming the microplasma chamber with the first and second electrodes being disposed circumferentially with respect to the tube and longitudinally disposed from one another.

The electrodes may be tubular electrodes with one of the electrodes forming an inlet conduit and the other of the electrodes forming an outlet conduit.

The miniaturized plasma device may further include a second tube for forming a second microplasma chamber, the second tube being connected to the first tube and sharing a common electrode; and, a third electrode being disposed circumferentially near the end of the second tube opposite the end of the second tube that is connected to the first tube, wherein the third electrode provides as an inlet conduit and the electrode at the end of the first tube not connected to the second tube provides an outlet conduit.

Alternatively, the miniaturized plasma device may further include: a second tube for forming a second microplasma chamber, the second tube being connected to the first tube and sharing a common electrode; and, a third electrode being disposed circumferentially near the end of the second tube opposite the end of the second tube that is connected to the first tube, wherein the third electrode and the electrode at the end of the first tube not adjacent to the second tube provide outlet conduits, and the common electrode includes an inlet for receiving the sample analyte and two outlets for providing the sample analyte to each microplasma chamber.

The power supply may be a battery that provides a voltage input in the range of 1 to 20 Volts.

The power supply may be an AC power supply operating in the frequency range of 1-300 kHz.

In another aspect, at least one embodiment of the invention provides a miniaturized sample introduction device for preparing a sample analyte gas. The miniaturized sample introduction device comprises: a sample holder including: a support; a coiled-filament disposed on the support for receiving the sample analyte; and, electrical wires running along the support and connected to the coiled-filament; a vaporization chamber including: an aperture for receiving the sample holder; a single inlet aperture for receiving a carrier gas; and, a single outlet for venting the sample analyte gas; a seal for sealing the vaporization chamber after the sample holder has been placed in the vaporization chamber; and, a power supply connected to the coiled-filament via the wires for applying power to the coiled-filament to dry and vaporize the sample analyte for producing the sample analyte gas.

In another aspect, at least one embodiment of the invention provides a measurement device for analyzing a sample analyte. The measurement device includes a sample introduction device for preparing the sample analyte; a microplasma source device connected to the sample introduction device for receiving the sample analyte and generating a microplasma; and, an analysis device connected to the microplasma source device for receiving and analyzing the microplasma.

The analysis device may include one of a quadrupole, ion trap, time-of-flight and magnetic section mass spectrometer.

The sample introduction device may be one of an ITV, mini-ITV, micro-ITV, cold vapor generation device, a micro-nebulizer coupled with a Nafion desolvating tube, an electrothermal vaporization device, laser ablation, particle sample introduction and spark ablation.

The analysis device may include a monochromator, a photomultiplier tube and analysis electronics.

The microplasma device may be a tandem microplasma device having two microplasma chambers.

The analysis device may further include an excitation light source, a spectrometer and analysis electronics.

The microplasma source device may be battery operated and, the analysis device may include a portable optical spectrometer coupled via fiber optics to the microplasma source device.

Alternatively, the analysis device includes a mass spectrometer and an optical spectrometer for simultaneously measuring emission of analyte photons.

BRIEF DESCRIPTION OF THE DRAWINGS

For a better understanding of the invention and to show more clearly how it may be carried into effect, reference will now be made, by way of example only, to the accompanying drawings which show at least one exemplary embodiment of the invention and in which.

DETAILED DESCRIPTION OF THE INVENTION

Figure 1:
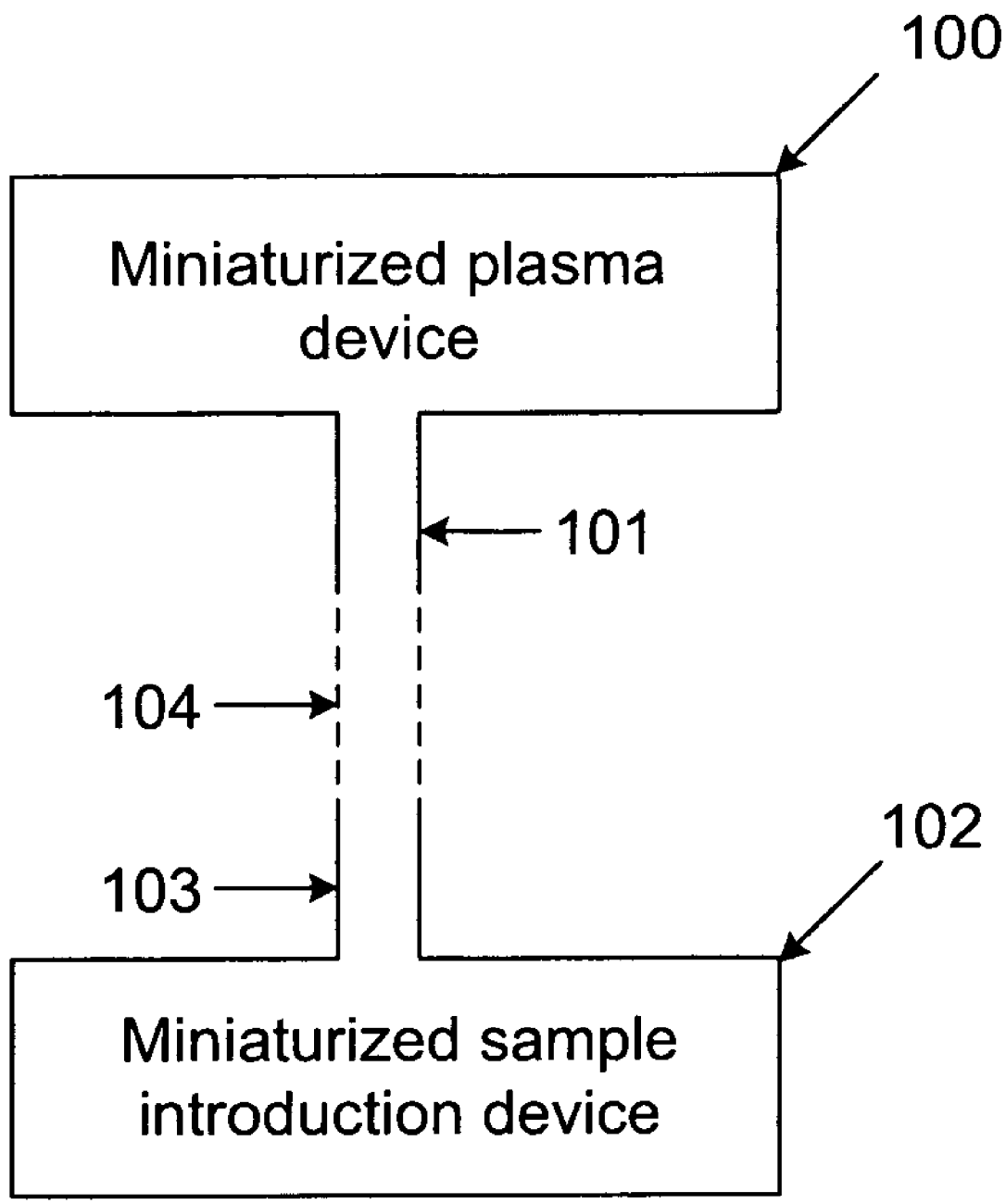
FIG. 1 is a schematic block diagram of an exemplary embodiment of a miniaturized plasma device and a miniaturized sample introduction device in accordance with the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements. In addition, numerous specific details are set forth in order to provide a thorough understanding of the invention. However, it will be understood by those of ordinary skill in the art that the invention may be practiced without these specific details. In other instances, well-known methods, procedures and components have not been described in detail so as not to obscure the invention.

As a first step for developing miniaturized plasma sources and plasma devices, pneumatic nebulizers will be considered. Can a pneumatic nebulizer be used to introduce liquid samples into miniaturized, low-power (i.e., 10 Watts or less) plasma sources? As power decreases from kW to W, is there sufficient energy to sustain such plasmas or will a low-power plasma be extinguished? These questions will be addressed by considering the steps that take place as a sample is carried from its container (e.g. beaker) to a plasma source and by estimating the energy required for each step. An exemplary list of steps is now provided. A liquid sample is first converted into wet aerosol droplets or a fine mist (i.e. it is nebulized). The wet aerosol droplets are then sorted according to their diameter (typically using a spray chamber) and a narrow range of aerosol droplets is introduced into the plasma source. The sorted droplets are then desolvated (i.e. the solvent is removed by vaporization) in the plasma source. The desolvated sample is then vaporized. Analytes (and a matrix) of the vaporized sample are then atomized and the gas phase atoms so generated are excited and/or ionized. Gas phase atoms or ions are probed using optical spectrometry or mass spectrometry (as is commonly known to those skilled in the art).

The power budget per step for the exemplary process listed above will now be discussed. Consider for example that an element somewhere around the middle of the periodic table is the analyte (to simplify calculations, a fictitious atomic weight of 100 is chosen). Furthermore, assume that a 1,000 ppm aqueous solution of a single element standard solution is introduced into a plasma source using a pneumatic nebulizer with a (typical) 1% sample introduction efficiency and an assumed flow-rate of 1 mL/min. Further assume that the energy required to desolvate this analyte is negligible. Also assume that the energy required to vaporize this hypothetical element from its salt is a modest 100 kcal/mol, that atomization (or salt dissociation energy) is about 200 kcal/mol, and that the excitation energy is about 200 kcal/mol (e.g., an excitation potential in the neighborhood of 8 eV). Then the total energy required to vaporize, atomize and excite this hypothetical analyte is calculated to be under 10 mW. Further assume that a negligible amount of energy is used to vaporize the water entering the plasma source. Since 99.9% of the 1,000 ppm sample is water solvent, then the energy required to fully dissociate the water solvent into two hydrogen atoms and one oxygen atom and to raise the temperature of the products of dissociation to about 5,000 K (as would be expected for an ICP source) is estimated to be about 10 W. From the large number of simplifying assumptions, it can be concluded that approximately 10 W of power are required for all of these steps. Using a more rigorous detailed approach, Olesik [Applied Spectroscopy, 51, 158A-175A, 1997] calculated that it actually takes about 30 Watts of power to perform these steps. The estimations and calculations outlined above are also supported by experimental evidence. For instance, it is known that plasmas cannot tolerate large water loads since they are simply extinguished. Even a 1 kW ICP source can be extinguished if any amount of water vapor is rapidly introduced into it.

From the example above, it can be concluded that the use of a pneumatic nebulizer for sample introduction into miniature plasmas is impractical since such plasmas are extinguished (as also observed experimentally). An alternative conclusion is that the water solvent must be removed (resulting in a "dry" sample) prior to sample introduction into low-power miniature plasmas. But even with the use of dried samples, could miniature plasmas operating at low power levels have sufficient energy density to provide acceptable analytical performance? This can be determined with the following order-of-magnitude calculation.

Consider, for example, a laboratory-scale 1 kW ICP with a fixed-volume (as dictated by the dimensions of the conventional plasma torch) of about 10,000 mm$^3$ as an example. A 1 kW ICP source has a power density of approximately 0.1 W/mm$^3$ (or 100 W/cm$^3$). Consider now a rectangular microplasma source with dimensions of 1.5 mm×5 mm×150 μm (W×L×D) operating at 0.1 W of power. The volume of this device is 1.125 mm$^3$. Such a microplasma device also has a power density of approximately 0.1 W/mm$^3$ which is the same as its larger scale counter-part. For miniaturized plasma sources, the power density can be easily changed; for instance, it can be made larger (by a considerable margin, if required) than that of an ICP source by simply increasing the power from milli-watts to watts or by decreasing volume (or by changing both simultaneously). Provided that energy density is directly related to analytical performance (and in particular to detection limits), microplasma sources can be made to perform as well, if not better, than conventional-size ICP sources. Further, if miniaturized plasma sources can be self-igniting and operate at atmospheric pressure so that there is no need for a vacuum pump then miniature plasma instrumentation is considerably simplified and portable compared to corresponding conventional large-scale analytical equipment. However, use of relatively low power (e.g. 10 W or less) necessitates the use of dry samples. Therefore, a low flow-rate, battery-operated sample introduction device that is compatible with miniaturized plasma sources is needed that can deliver dry samples. Such a device is discussed further below.

Referring first to FIG. 1, shown therein is a schematic block diagram of an exemplary embodiment of a miniaturized source comprising a miniaturized plasma device 100 having an inlet 101 and a miniaturized sample introduction device 102 having an outlet 103. The miniaturized plasma device 100 and miniaturized sample introduction device 102 may collectively be referred to as a miniaturized sample source. The miniaturized sample source is unique in comparison to previous sample sources because this is the first time that a miniaturized sample introduction device has been specifically developed for a miniaturized source and vice-versa. The other unique feature is that the plasma source and sample introduction devices are both miniaturized. The outlet 103 of the sample introduction device 102 is connected to the inlet 101 of the miniature plasma device 100. Samples are deposited into the miniaturized sample introduction device 102 and then introduced into the miniaturized plasma source 100. The dashed line indicates that an additional tube 104 may be optionally connected in between the outlet 103 and the inlet 101. In the case of the additional tube 104, the outlet 103 and the inlet 101 are preferably located as close as possible (to within a few tens of millimeters) to one another. The tube 104 has been added to simplify the interface, which is quite useful depending on the configuration of these devices 100 and 102 as will be shown further below.

Figure 2:
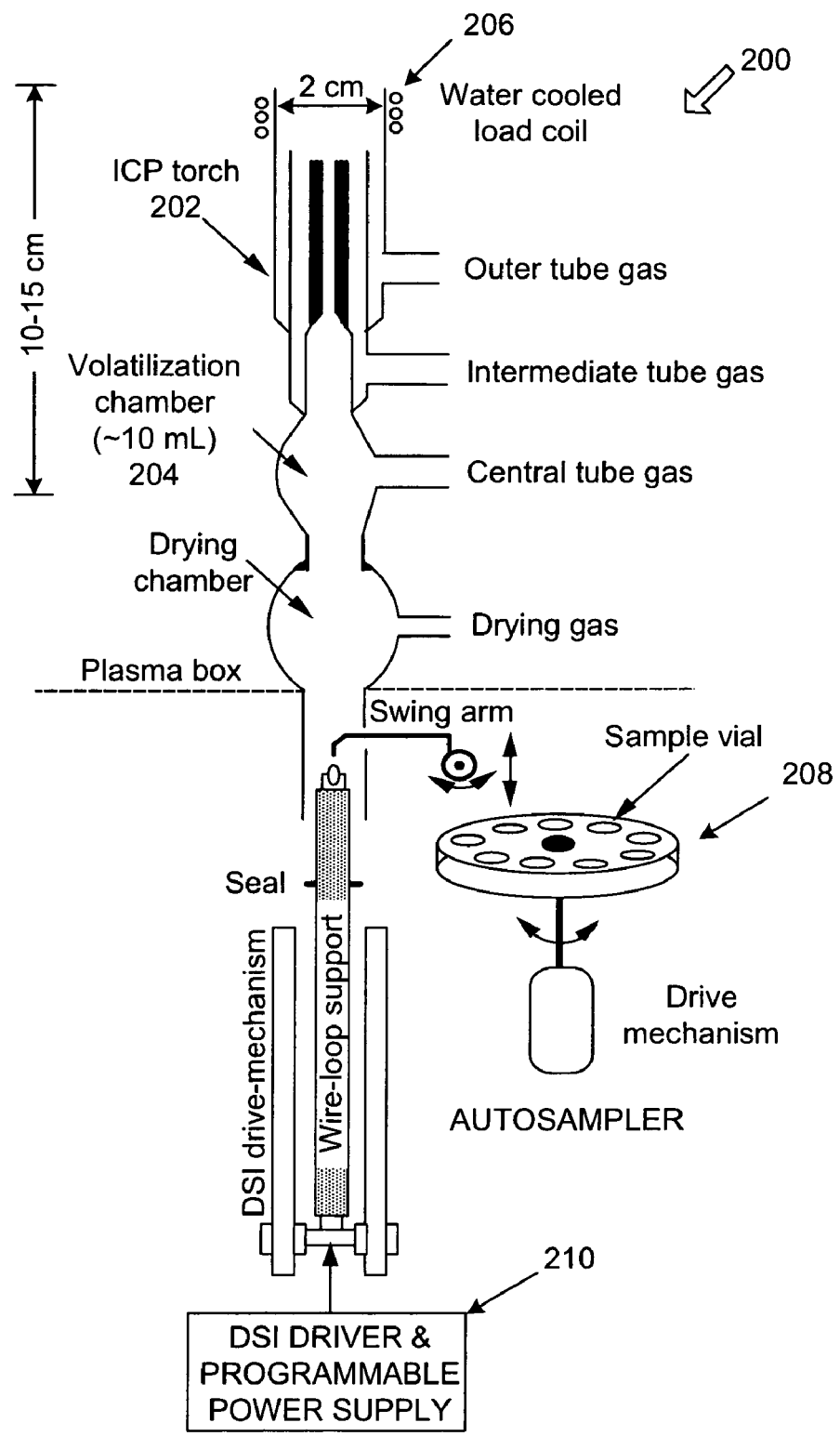
FIG. 2 is a schematic diagram of a conventional ITV device.

Referring now to FIG. 2, shown therein is a schematic diagram of a conventional in-torch vaporization (ITV) sample introduction device 200 that can be used to provide micro or nano-size amounts of a sample to a laboratory scale plasma source for elemental analysis. The ITV sample introduction device 200 is described in more detail in U.S. Pat. Nos. 5,705,787 and 6,184,982. Typical dimensions for the size of the plasma torch 200, the volume of the volatilization (i.e. vaporization) chamber 204 and the water-cooled load coil 206 have been included. The ITV sample introduction device 200 allows for a small amount of a liquid sample to be deposited onto a sample-carrying probe 208, such as a wire-loop. Alternatively, a metal cup can also be used. Although different metals (e.g. W, Re, Ta, Mo) can be used to make wire-loops or metal cups, Rhenium (Re) is the preferred material. The sample-carrying probe 208 is secured on top of a metallic or a ceramic support. Cables running through holes in the support (not shown) connect the sample-carrying probe 208 to an electrical power supply 210. In typical operation, a liquid sample is pipetted onto the probe 208 and the probe 208 along with the support is inserted into the modified plasma torch 202 with the built-in volatilization (or vaporization) chamber 204 having a volume of about 10 cm$^3$. Low electrical power is applied to the probe 208 for about 60 to 90 seconds to dry the sample. A higher power level is then used to pyrolyze any organics that may be present in the sample and an even higher power level is used to vaporize the sample residue that remains in or on the probe. The vaporization lasts under a second but is typically monitored for about 5 seconds. Typical ITV power levels range between 0.6 and 50 W with an upper maximum power of about 120 W. Once vaporized, a carrier-gas with an overall optimum flow rate of about 0.65-0.85 L/min transports the vaporized sample from the volatilization chamber 204 to an ICP source for further vaporization, atomization and excitation (for optical emission measurements), and ionization (for measurement by mass spectrometry). The carrier-gas flow-rate enables the ITV sample introduction device 200 to be compatible with conventional-size ICP sources for measurement by ITV-ICP-AES (ITV-ICP-Atomic Emission Spectrometry) or ITV-ICP-MS (ITV-ICP-Mass Spectrometry) methods. The carrier-gas flow rate is critical for optimum performance of the ITV sample introduction device 200 since the volatilization chamber 204 relies on the formation of a vortex to deliver optimum performance. The vortex helps to confine vaporized samples in the center of the chamber 204, thus preventing hot (e.g., 2000-3000° C.) analytes from adhering to the cold walls of the chamber 204 and not being available for further analysis. Low flow-rates (e.g., below about 0.5 L/min) and high flow-rates (e.g., above 1.2 L/min) are thought to adversely affect (and perhaps even destroy) the vortex, thus adversely affecting analytical performance characteristics, for example by degrading detection limits. However, at its optimum flow-rate, the vaporization chamber 204 has about 100% efficiency, thus improving ICP detection limits by about two-orders of magnitude compared to instruments which use pneumatic nebulization sample introduction. Additionally, because small amounts of solid samples can be deposited on the sample-carrying probe (for example, as water-based slurries), the need for acid digestion is eliminated. The optimum carrier-gas flow-rate for the ITV sample introduction device 200 is also optimum for ICP operation as well, but it is incompatible with miniature, low flow-rate (30-350 mL/min) plasma sources.

To obtain optimum analytical performance, compatibility with low-flow rate (e.g. below 0.5 L/min) and maximum sample introduction efficiency for interface with a miniaturized plasma source, the inventor has found that the size of the ITV sample introduction device 200, along with the flow-rate and power consumption of the device 200, can be reduced to provide one exemplary implementation of the miniaturized sample introduction device 102. The inventor has found that coupling a miniaturized ITV sample introduction device to a miniature plasma source offers several benefits compared to the large-scale TV device 200. For example, a low duty cycle of about a sample-a-minute can be used which means that both the miniaturized plasma device 100 and the carrier-gas flow-rate can be turned off when the sample is drying. This intermittent miniaturized plasma operation conserves power and reduces gas consumption even further, thus promoting portability. Due to this intermittent operation, a small and relatively light-weight compressed-gas cylinder can be used to provide support gas for the miniaturized plasma device 100 and such a cylinder can be attached, for instance, to the belt of a worker (akin to a tool belt), thus enabling portability. Such gas cylinders are commercially available and can provide support gas for approximately eight hours of operation.

Another issue to consider is that plasma sources get hot during operation. However, since vaporization typically lasts under a second and the plasma source is typically monitored for 5 seconds, the inventor has realized that the miniature plasma device 100 can be turned on for a brief period of time thereby permitting intermittent operation. With intermittent operation, the miniaturized plasma device 100 barely gets warm and can be safely touched. Thus, with intermittent operation heat-dissipation and cooling are non-issues. Overall, a miniaturized ITV sample introduction device facilitates intermittent operation of the miniaturized plasma device 100. Further, since heating is not an issue, water-cooling is not required which further increases the portability of the miniaturized plasma device 100 and the miniaturized sample introduction device 102.

Figure 3:
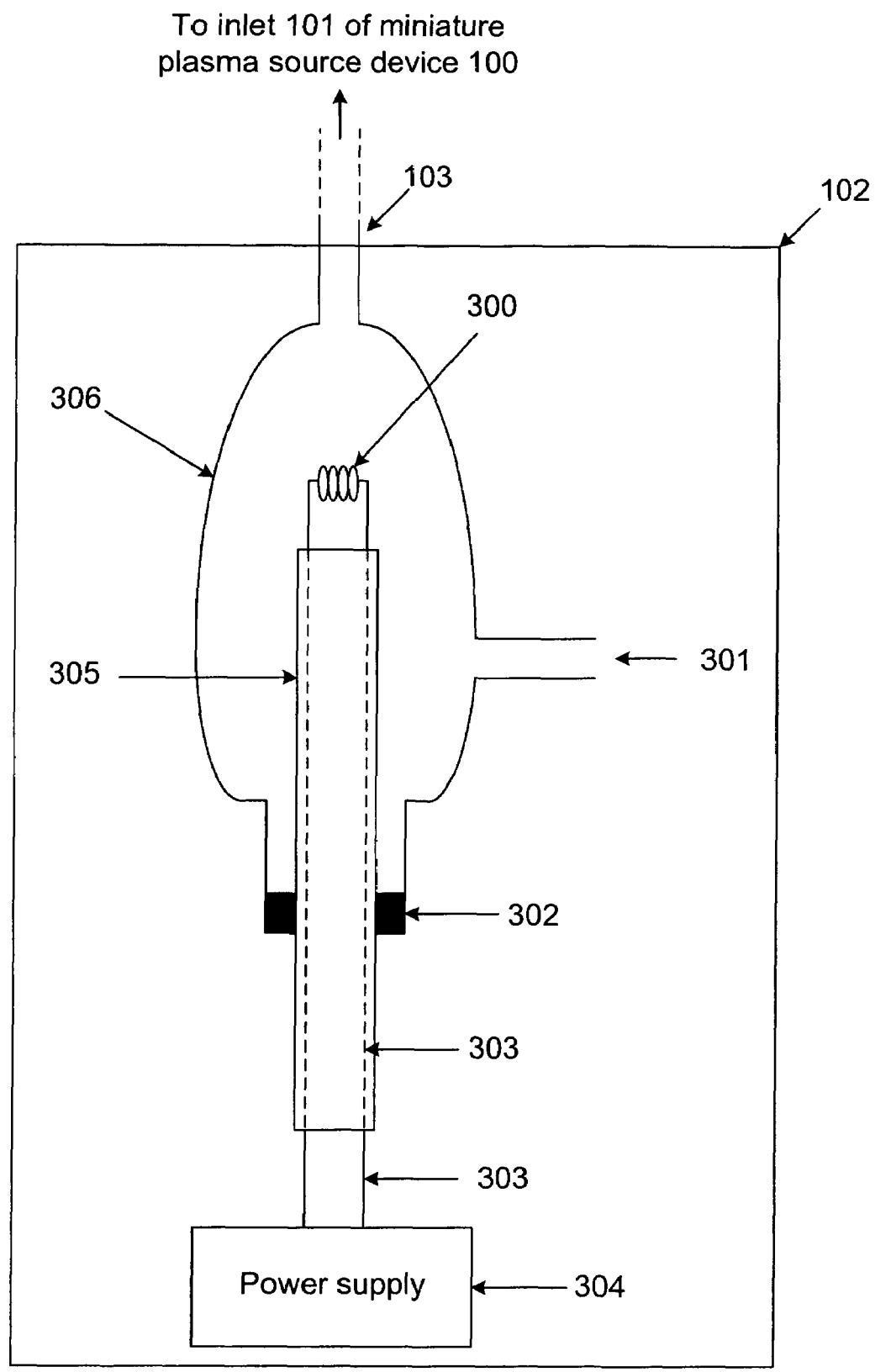
FIG. 3 is an exemplary embodiment of a miniaturized ITV device in accordance with the invention.

Referring now to FIG. 3, shown therein is an exemplary embodiment of a miniaturized ITV (i.e. mini-ITV) sample introduction device in accordance with the invention. A small sample is deposited onto a coiled-filament 300 positioned inside a small-volume (e.g. 1-3 mL) vaporization chamber 306. The vaporization chamber 306 has been designed to operate between 100-300 mL/min, with an optimum flow-rate of about 250 mL/min. The vaporization chamber 306 includes an input conduit 301 for receiving carrier gas flow and an output conduit 103 for providing the sample gas. Electrical cables 303 running through a support 305 connect the coiled-filament 300 to a power supply 304. The support 305 is made from a heat insensitive material such as ceramic for example. In one embodiment, the power supply 304 is preferably computer-controlled and battery-operated. Although different metals may be used (such as W, Ta, Mo, or Pt), the filament is preferably made out of thin Re wire having a diameter or 25 μm (or less). To simplify the description, the combination of the support 305, cables 303 and the coiled filament 300 will be referred to as a sample holder. The sample holder is removable and a seal 302 is used to seal the vaporization chamber 306 when the sample holder is placed within the vaporization chamber 306. With the bottom of the vaporization chamber 306 sealed and the outlet 103 of the vaporization chamber 306 connected to the inlet 101 of a miniaturized plasma device 100, the carrier-gas (301) flow-rate also becomes the plasma (100) gas flow-rate.

There are significant differences between the sample introduction approaches shown in FIGS. 2 and 3. As shown in FIG. 2, a drying chamber is part of the system. The miniaturized device shown in FIG. 3 has no drying chamber and it only has one input (301). In addition, the vaporization chamber (with a volume of 6-10 mL, FIG. 2) is built into a large size ICP torch. However, in the vaporization chamber 306 shown in FIG. 3 (with a volume of 1-2 mL), there is no ICP torch. Importantly, there are significant differences in carrier-gas flow-rates (as mentioned above) thus making conventional size ITV unusable with miniaturized plasma devices. Conversely, carrier-gas flow-rate (301) incompatibilities make a miniaturized ITV unusable with ICP torches. In fact, to accommodate flow-rate requirements of microplasma devices with progressively smaller diameter (or cross-section) channels, a mini-ITV (with an optimum flow-rate of about 250 mL/min) and a micro-ITV (with the vaporization chamber having a volume of about 250 µL and an optimum flow-rate of 30 mL/min) have been developed. Development of mini- and micro-ITV devices was non-trivial, these were developed using commercially-available computational fluid dynamics software as a guide. Such software is used, for example, to simulate gas flows around the wings of aircraft or for development of more fuel-efficient automobiles with reduced aerodynamic drag. Additional differences between conventional size ITV and miniaturized ITV devices will be highlighted in the following sections as well as flow-rate compatibilities.

In typical operation, the sample holder is removed from the vaporization chamber 306 so that a few µL of sample (e.g. 1-5 µL) can be added to the coiled-filament 300. The sample holder is then re-inserted into the vaporization chamber 306. The bottom of the vaporization chamber 306 is then sealed with the seal 302. The outlet 103 of the vaporization chamber 306 is disconnected from the miniaturized plasma device 100 (which is switched off) and low electrical power (e.g. 0.5 W) is applied to the sample carrying coiled-filament 300 to dry the sample on it. The outlet 103 is disconnected from the inlet 101 for eliminating possible water condensation in the plasma device 101. After a time period of about 60-90 seconds, a dried sample residue remains on the coiled 300 filament. The outlet 103 is then re-connected to the inlet 101 of the miniaturized plasma source 100. The gas flow source (not shown) which provides carrier-gas flow to the input conduit 301 is then switched on to provide a flow-rate of about 250 mL/min. The carrier-gas flow also serves as a support plasma-gas for the miniaturized plasma device 100. The plasma device 100 is then switched on. A higher amount of electrical power (with a maximum of about 10 W) is then provided from the power supply 304 to the sample-carrying filament 300. The dried sample residue on the coil 300 is vaporized and the carrier-gas carries the vaporized sample into the miniaturized plasma device 100. This vaporization event lasts for under about a second, and the plasma that is then formed in the miniaturized plasma device 100 is monitored for about 5 seconds. The miniaturized plasma device 100, the carrier-gas source and the power supply 304 are then switched off.

Figure 4:
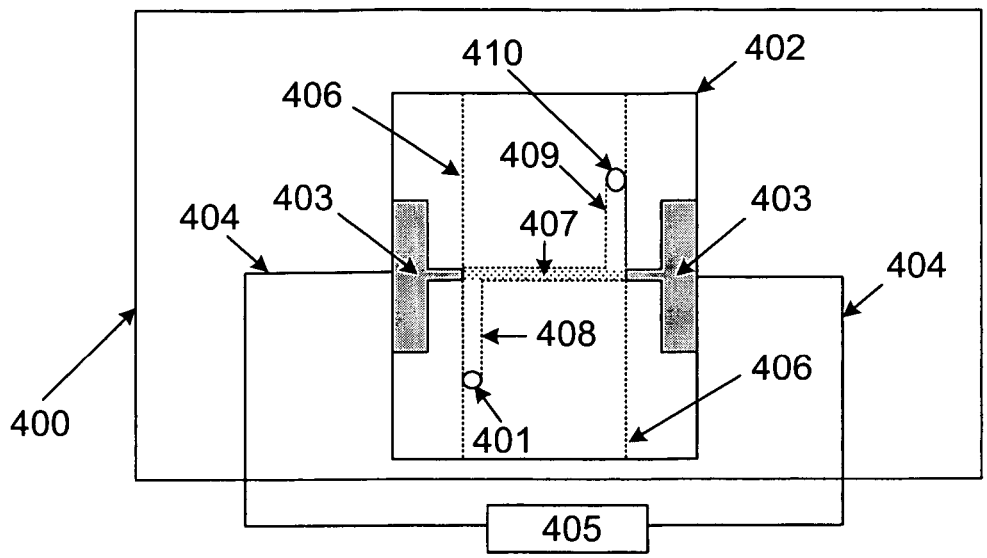
FIG. 4 is a top view of an exemplary embodiment of a planar microplasma device (abbreviated as MPD) in accordance with the invention.
Figure 5:
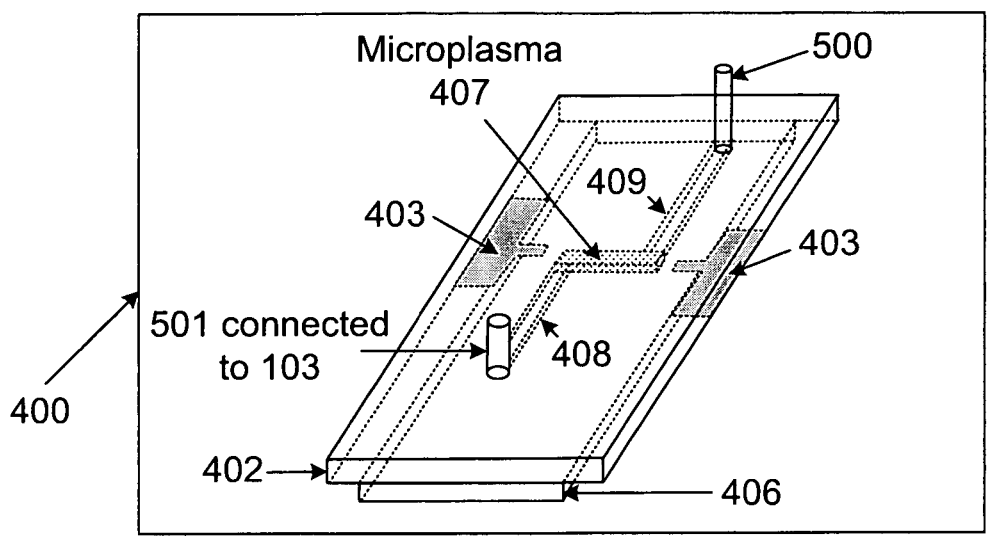
FIG. 5 is an isometric view of the planar microplasma device of FIG. 4.

Referring now to FIGS. 4 and 5, shown therein is a top view and an isometric view, respectively, of an exemplary embodiment of a planar microplasma device 400 that may be used as the miniaturized plasma device 100 in accordance with the invention. The planar microplasma device 400 has exemplary dimensions of about 25.4 mm by 50.8 mm. The microplasma device 400 includes a first or top wafer 402 and a second or bottom wafer 406. The wafers 402 and 406 may be formed using glass, quartz, transparent polymeric materials such as commercially available polyethersuulphone (PES), polyethylnapthalate (PEN) or polyester (PET). Other suitable materials may also be used. On the top surface of the bottom wafer 406 there is a microchannel 407 which, for example, may be 5 mm long, 1 mm wide and 250 µm deep. There are also two channels 408 and 409 that are in fluid communication with the microchannel 407. Microchannel 407 serves as a microplasma chamber where the plasma is created. The depth of channels 408 and 409 may be the same as that of the main channel 407. Depending on the particular device, the length of channels 408 and 409 may be varied from about 5 mm to about 10 mm. In this example, the channels 408 and 409 are perpendicular to the main channel 407. Although not shown in FIGS. 4 and 5, the wafers 402 and 406 may be separated by insulating spacers made out of glass, quartz or transparent polymeric material and may be several hundred micrometers (preferably 500 µm) or a few millimeters tall. It should further be noted that the microchannels 407, 408 and 409 do not have to be rectangular. Other shapes may be used such as semicircular (for the cross-sectional profile). Tapering the channels might also be useful. The channels may be microfabricated as follows. They may first be defined using photo lithography and can then be subsequently etched using wet chemical etching. One example of such chemical etching is described in V. Karanassios and J. T. Sharples, "Microchannels and microcells for gaseous microsamples", Sensors and Materials, 9, pp. 363-378, 1997, and V. Karanassios and G. Mew, "Anisotropic wet chemical etching of Si for chemical analysis applications", Sensors and Materials, 9, pp. 935-416, 1997 which are both hereby incorporated by reference.

On the back surface of the bottom wafer 406, holes 401 and 410 were drilled at the end of the channels 408 and 409. These holes had the same diameter as channels 408 and 409. Glass or plastic tubes 500 and 501 of appropriate diameter were affixed to holes 401 and 410 such that the diameter of the tube preferably matched the width of the microchannel to which it was attached. For instance, a 100 µm channel had a 100 µm tube, an 800 µm channel was connected to an 800 µm tube and so on. The tube 501 affixed to hole 401 served as an inlet and it communicated with outlet 103 of the miniaturized sample introduction system 102. The tube 500 affixed to hole 410 served as an outlet and it was left open to the atmosphere. Alternatively, it could have been connected to another device. The tubes 500, 501 were placed within the channels 409, 408 such that either they had apertures that opened up into these channels 409, 408 or they were placed slightly higher than the floor, but still within the sidewalls, of the corresponding channels 409, 408 to provide fluid communication therewith. The tubes 500, 501 also extended up through corresponding holes in the top wafer 402 so that a portion of the tubes 500, 501 extended past the top surface of the top wafer 402 to permit connection to another device (501) or to serve as outlet (502). The wafers 402 and 406 may be bonded together or otherwise secured to one another; in some cases glue may be used.

On the front surface of the top wafer 402, thin film (less than 1 µm) electrodes 403, preferably gold, were photo lithographically defined and sputter deposited. Other metals such as Ni, Cr, Ta, Mo or Au may also be used. Further, the electrodes are preferably covered with a thin film (i.e. 1 um or less) of a suitable dielectric material such as $S_xO_2$. Each electrode 403 has a long outward portion and a narrow inward portion. The longer portions of each electrode 403 serve as electrical contact pads that are connected to cables 404 that carry electrical power from a power supply 405. The wafer 402 with the electrodes 403 is positioned so that the surface with the electrodes 403 was facing the etched surface of the bottom wafer 406 having the channels 407, 408 and 409. The wafer 402 is also positioned so that the narrow ends of the electrodes 403 are facing and substantially inline with the main channel 407. The electrodes may be made to be 0.5-5 mm wide. The interelectrode distance (i.e. horizontal distance between them) may be between 1 μm and 100 mm and is preferably 20 mm.

In use, a microplasma (having a volume on the order of micro-liters) is formed in the main channel 407 between the electrodes 403. In essence, the main channel 407 serves as a plasma chamber. The electrodes 403 provide electrical power to the main channel 407 for generation of the microplasma. In one instance, an operating voltage of approximately 3 kV to 4 kV DC may be applied to the electrodes with a resistor being connected between the power source 405 and one of the electrodes to ballast the discharge. There are low voltage DC (e.g., 5 V) power supplies that can convert, provide a voltage as high as 10,000 Volts (DC) and the power supplies are the size of a match box. These power supplies are commercially available. To eliminate sputtering of the electrodes 403, an AC power supply rather than a DC power supply may be used for the power source 405. The AC power supply may operate at a frequency between 1 Hz to 100 GHz with the range 1-300 kHz being preferable. For instance, the ac power supply may operate at a frequency of 35 kHz.

Several variations may be made to the miniaturized plasma device 400. For instance, the width, depth and length of the microchannels 407, 408 and 409 may be varied to vary the microplasma volume, which in some cases may be on the order of nano-liters. In addition, the geometry of the electrodes 403 may be changed to a triangular shape in which the base of the triangle faces the outer edge of the wafer 402 and the tips of the triangle face inwards and are substantially aligned with the microplasma chamber 407. The inner portions of the electrodes is narrower or tapered with respect to the base portion to concentrate the amount of charge in order to generate the microplasma.

In addition, the microchannels 408 and 409 can be etched at an angle to the main channel 407. This reduces the possibility of the sample collecting in the sharp 90° corners of the embodiment shown in FIGS. 4 and 5 which may potentially cause memory effects. Further, the lengths of the microchannels 408 and 409 can be varied. For instance, the lengths of the microchannels 408 and 409 may be selected so that the glass tubes 500 and 501 are situated within the longitudinal extent of the electrodes 403 and in some cases the narrow portion of the electrodes 403 (in this case the narrow portion of the electrodes 403 may be slightly extended). Moreover, rather than using gold to make the electrodes, another suitable metal may be used such as Cr, Ni, Ta, Mo or another appropriate sputter-target material. Also, the top wafer does not need to be larger than the bottom wafer. Both wafers may be the same size or the bottom wafer may also be larger than the top wafer.

The AC power supply that may be used as the power supply 405 may be operated at frequencies in the Hz to GHz range without deviating from the scope of the invention. Further, the power supply 405 provides power in the range of several milliwatts to about 10 W to the microplasma formed in the main microchannel 407. In one embodiment, inexpensive power supplies similar to those used for powering plasma globes or neon signs may be used. They operate between 25-40 kHz and are powered by a battery (at present, using a portable, commercially available, re-chargeable drill battery). Overall, operation in the kHz range is preferred because at these frequencies an impedance matching network between the power supply and the miniaturized plasma device is not required, thus instrumentation is simplified and cost and weight are reduced. The power supply is of similar size and weight as, for example, the transformer found in typical fluorescent lights and has been used to initiate and sustain plasmas in a variety of gases and gas mixtures, such as Ar, Ar—$H_2$, He—$H_2$, Ne, Kr, Xe, $N_2$ or air.

Reducing the size of the channels 407, 408 and 409 reduces the flow-rate of the carrier-gas that passes through them. However, when the flow-rate decreases, the vortex in the mini-ITV vaporization chamber 306 is destroyed, thus degrading analytical performance characteristics. This effect may occur for a cross-section of approximately 1 $mm^2$. To address this issue, for microplasma devices having small channels that reduce the carrier gas flow, the inventor developed a micro-ITV sample introduction device, similar to that shown in FIG. 3 but with a micro-vaporization chamber having a volume of about 250 μL. The micro-vaporization chamber can be operated with carrier-gas flow-rates as low as 10-100 mL/min. The inventor has found that an optimum flow-rate is about 30 mL/min. The micro-ITV may be used with decreased flow-rates compatible with microplasma devices having very small micro-channels. The mini-ITV and micro-ITV further allow one to use a variety of microplasma devices in which the size of the inlet, outlet and microplasma channels gets progressively smaller. This may be advantageous when dealing with certain sizes of liquid or solid micro-samples.

Figure 6:
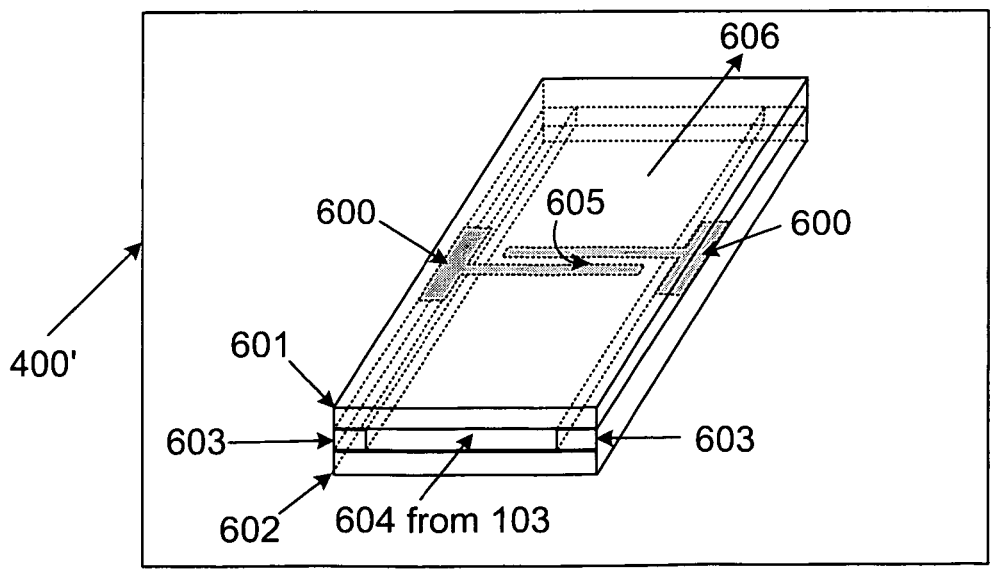
FIG. 6 is an isometric view of an exemplary embodiment of an alternative planar microplasma device in accordance with the invention.

To demonstrate flexibility in forming and sustaining microplasmas with microplasma devices having different geometries another exemplary embodiment will be discussed. Referring now to FIG. 6, shown therein is an isometric view of an alternative planar microplasma device 400' in accordance with the invention. The microplasma device 400' includes electrodes 600, which in this example were made from Cr, on a top wafer 601 and a bottom wafer 602. The wafers 601 and 602 are made from quartz and have a dimension of 25.4 mm by 50.8 mm. The inventor has found that it is the channel size and distance between the electrodes that matters with this embodiment. The electrodes 600 were sputter-deposited on the wafers 601 and 602. In some cases, to prevent electrode oxidation, a thin film (<1 μm) of an appropriate insulator may be microfabricated on top of the electrodes 600 while covering the entire wafer. The electrodes 600 were positioned to face one another so one electrode 600 was placed on the bottom surface of the wafer 601 and the other electrode 600 was placed on the top surface of the wafer 602. The interelectrode distance (i.e. vertical height between them) may be between 1 um and 100 mm and is preferably 20 mm. Both electrodes 600 were connected to a power supply (not shown for clarity). Variations on materials used for the electrodes and wafers are the same as those given for the embodiment of FIGS. 4 and 5. Typically, the electrodes were 2 mm wide and the inwardly extending portion was about 10 mm long, but devices with different lengths and widths for the channel and the electrodes can be easily fabricated. The microplasma device 400' also includes side-walls or spacers 603 which run the length of the device 400'. The spacers 603 separate the top and bottom wafers 601 and 602, and accordingly the electrodes 600, from one another thus creating a microcavity or microchannel 604 within the microplasma device 400' with a channel inlet at one end and a channel outlet at the other end. The spacers also act as insulating layers and may be made out of glass, quartz or transparent polymeric material such as those compositions mentioned above. The inventor has found that the linear inlet-to-outlet geometry substantially reduces memory effects. The channel inlet is connected by appropriate means to the outlet 103 of the miniaturized sample introduction device 102. In this example, the spacers 603 have a height of about 500 µm. The pieces 601, 602 and 603 may be glued or otherwise bonded together. In use, a microplasma is formed in the region 605 between the opposite facing electrodes 600. Accordingly, the narrow tips of the electrodes 600 preferably overlap one another over the region 605 to create the microplasma. By changing the length, width and depth of the micro-cavity 604, microplasmas of different volumes ranging from 500 µL to tens of nL may be generated. In some cases, the microchannel may be tapered.

Figure 7:
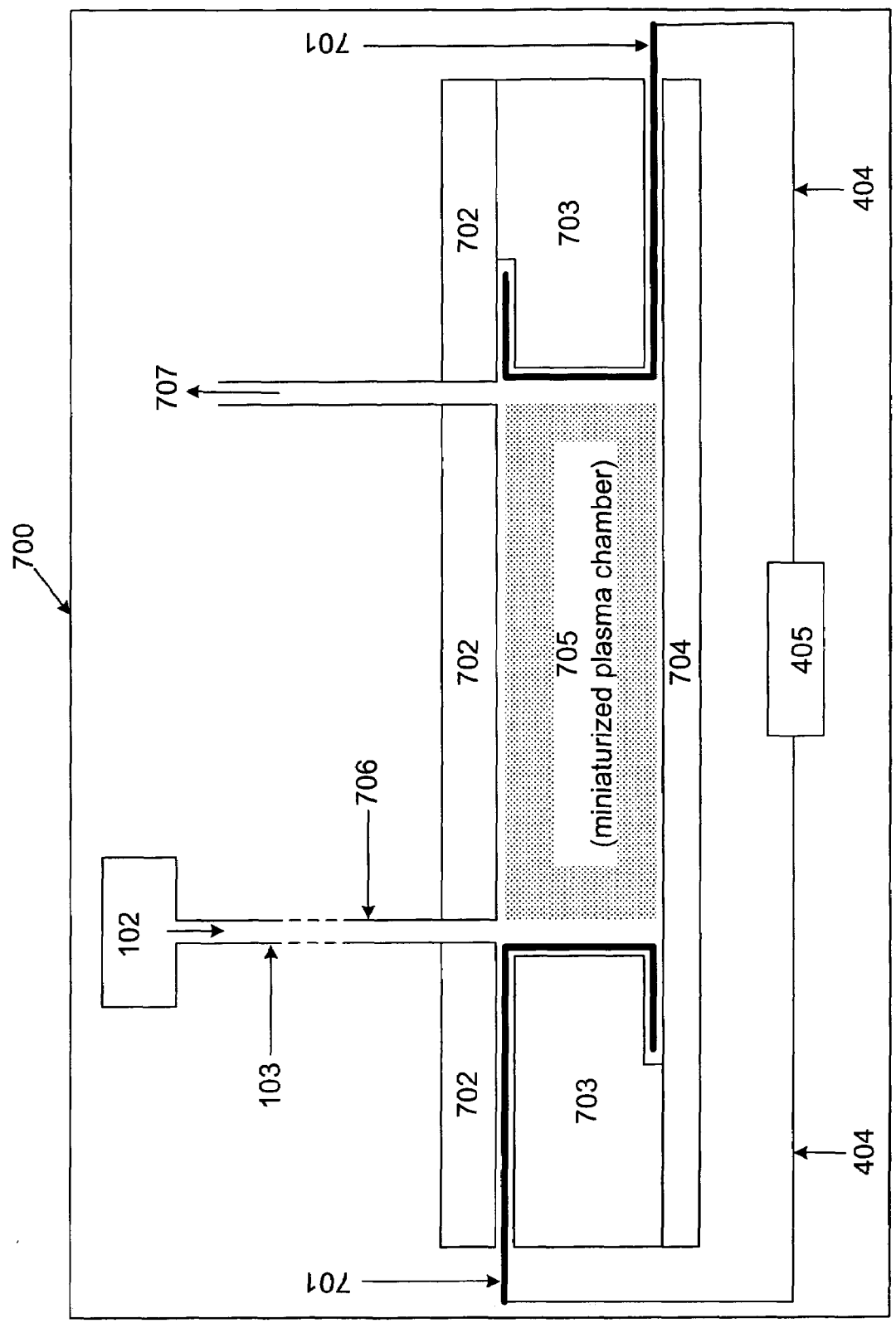
FIG. 7 is a cross-sectional view of an exemplary embodiment of another alternative planar microplasma device in accordance with the invention.

Referring now to FIG. 7, shown therein is a cross-sectional view of an exemplary embodiment of another alternative planar microplasma device 700 in accordance with the invention. In this example, electrodes 701 consisted of Mo, Ni or Cr strips that were 2 mm wide and several millimeters long. In other embodiments, the electrodes may be between 0.5 to 10 mm wide and may also be made from Ta, Pt or Au foil although Mo is preferable. The interelectrode distance is between 0.1 mm and 25 cm and is preferably between 20-30 mm. The typical electrode 701 thickness was 25 µm but it varied from 10 µm to several tens of micrometers. The miniaturized plasma was formed between three glass or quartz (25.4 mm by 50.8 mm) wafers 702, 703 and 704 that were bonded or glued together. Also included in the device are front and back wafers (not shown) to provide front and back walls to complete the microplasma chamber 705. The middle wafer 703 is defined and etched (as described previously) to accommodate the electrodes 701. Quartz is preferably used due to its desirable optical properties in the UV region (UV transparency is important because many elements such as Pb, Cd and Zn have their best spectral lines in this region of the spectrum). Molybdenum is preferably used to make the electrodes 701 due to its desirable work function (which makes miniaturized plasmas easier to initiate and sustain) and to its high sputtering threshold energy and low sputtering yield. Other materials may be used for the wafers as described previously for other embodiments.

The plasma is formed and sustained in the rectangular channel 705 that is formed between the electrodes 700 and the wafers 702, 703, 704 and the front and back wafers (not shown). The rectangular channel 705 may have volumes ranging from the nano-liter range to several thousands of micro-liters (typical dimensions were: 5 mm length, 500 µm height and 2 mm width). Similar to the embodiment 400, holes of an appropriate diameter (e.g. 1 mm) were drilled through the top wafer 702 and glass or plastic tubes 706 and 707 were affixed to the holes. Tube 706 transports the carrier gas (and the sample from the miniaturized sample introduction device 102) to the plasma chamber 705, and tube 707 provides an outlet. Cables 404 were used to connect the electrodes 701 to the power supply 405 for delivering power to the plasma chamber 705. Although dc and ac operation was tested, as mentioned before, ac operation is preferred to minimize electrode sputtering.

In a slight variation, the microplasma device 700 was provided with a collinear inlet-outlet geometry similar to that shown in FIG. 6 as opposed to the parallel inlet-outlet configuration of FIG. 7. Such a geometry was used in the development of collinear geometry miniaturized plasma on a plastic substrate using Mo strips as electrodes. Use of a plastic substrate also demonstrated that significant flexibility exists not only in device geometry but also in the types of materials that can be used as substrates.

Figure 8:
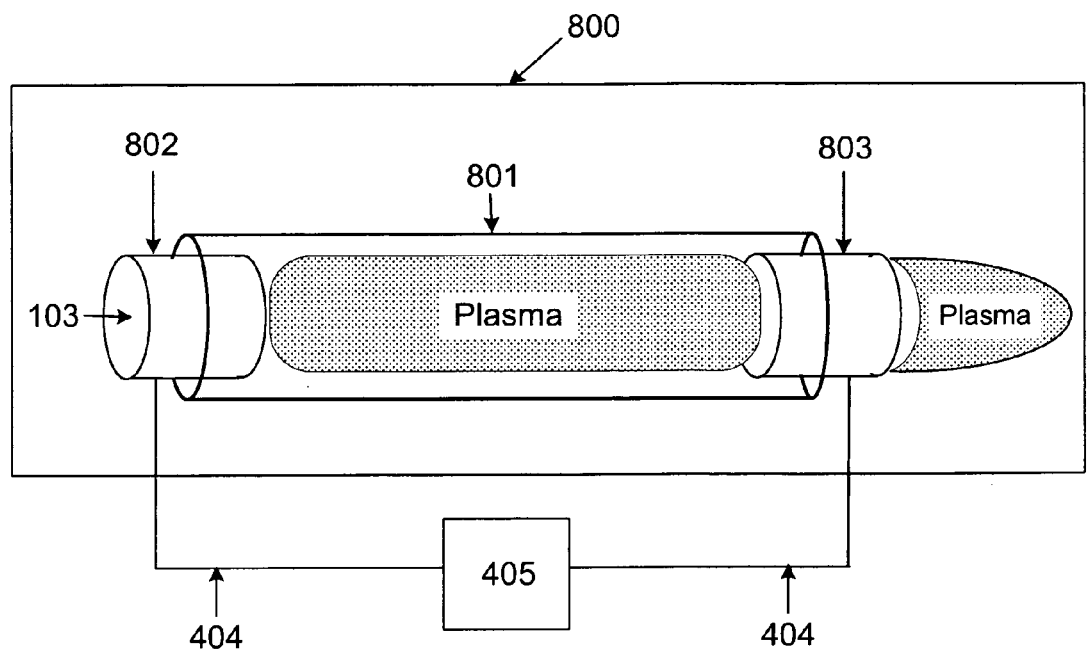
FIG. 8 is a schematic diagram of an exemplary embodiment of a tubular miniaturized plasma device in accordance with the invention.

Thus far, rectangular geometry plasma channels have been described. However, this need not be the case. Referring now to FIG. 8, shown therein is a schematic diagram of an exemplary embodiment of a tubular miniaturized plasma device 800 in accordance with the invention. The tubular device geometry is chosen to facilitate interfacing the miniaturized plasma device 800 with the round outlet (103) of miniaturized sample introduction devices (FIG. 3), such as mini-ITV or micro-ITV. Fortuitously, it also facilitated interfacing tubular-geometry microplasma devices to the round sampling cone of a conventional-size mass-spectrometer and as will be discussed later, such an interface proved to be invaluable. A unique advantage of tubular plasma devices is that while they maintain the microliter to sub-microliter volume advantage of the planar devices described in FIGS. 4-7, they are much easier and cheaper to produce in small quantities (thus reducing research and development cost) because they do not rely on microfabrication technology.

The tubular microplasma device 800 includes a tubular or cylindrical body 801 with open ends. The tube 801 may be made from glass, quartz, or transparent polymeric material such as PES, PEN or PET. The tube 801 has a diameter that varies between 2 mm to fractions of a millimeter with approximately 500 µm being preferable. Tubular electrodes 802, 803 are placed at either end of the tube 801. Short segments (e.g. 2-5 mm) of Mo tubes or stainless steel tubes (cut from hypothermic syringe needles) may be used for the electrodes 802, 803 with Mo being the preferred material. Other material that can be used for the electrodes 802, 803 include Ni, Cr, Ta, Pt or Au. The tubular electrodes 802, 803 may be made out of 0.01-4 mm diameter tubes and may be 1-10 mm long. The inter-electrode distance between the tubular electrodes is between 0.1 mm and 25 cm but preferably 20-30 mm. The tubular electrode 802 is in communication with the outlet 103 of the sample introduction device 102 and serves as an inlet for the device 800. The tubular electrode 803 provides an outlet for the device 800. The electrodes 802, 803 are connected to the power supply 405 via the cables 404. The power supply can be either dc or ac operated (although ac operation is preferred).

The flow-rate depends on the diameter of the tube 801, or the cross-sectional area (in this case defined as $\pi r^2$ where r is the radius of the limiting orifice of the tube which is typically the inner diameter of the tubular electrodes 802, 803. Also, when the outlet of a miniaturized ITV is connected to the inlet of the microplasma device 800, as the diameter of the limiting orifice decreases, a back pressure develops inside the vaporization chamber of the miniaturized ITV device. Such a back pressure destroys the vortex inside the chamber thus significantly degrading analytical performance. Thus, it is important not to generate a back pressure. In other words, from the point of view of flow-rate point, the microplasma device and the microsample introduction device must be designed to be compatible with one another. Accordingly, the use of a mini-ITV or a micro-ITV depends on the limiting inner diameter of the tubular electrode and on gas pressure. As a rough rule of thumb, the transition from a mini-ITV to a micro-ITV for typical gas pressures used for flow-rate (and as a consequence from plasma gas) occurs when the diameter of the tubular electrode is around 500 µm.

The length of the tube 801, and hence the distance between the electrodes 802, 803 can be varied from the sub millimeter range to as much as 25 cm for example. The length of the tube is preferably about 20 mm. By increasing the length of the tube 800, the residence time of the analytes within the plasma is increased. This is beneficial since increasing the residence time provides more time for the analytes to interact with the plasma thus potentially offering improved analytical performance.

Improved analytical performance is also obtained by reducing the length of the tube though which a vaporized sample has to travel from the outlet 306 of the vaporization chamber 103 to reach the miniaturized plasma device (100). By reducing the length of this tube, the likelihood of analyte loss to the walls of the tube is reduced or eliminated. As mentioned before, use of tubular-geometry electrodes facilitates interfacing between a miniaturized plasma device and a miniaturized sample introduction system. Such a tightly integrated miniaturized device-miniaturized sample introduction system facilitates portability even further. Various embodiments along these lines are shown in FIGS. 9-12. In the embodiments shown in these figures, electrical power from power supply 405 is transferred to a miniaturized plasma device using cables 404. Although the miniaturized plasma devices can be operated in dc or ac mode, ac operation is preferred.

Figure 9:
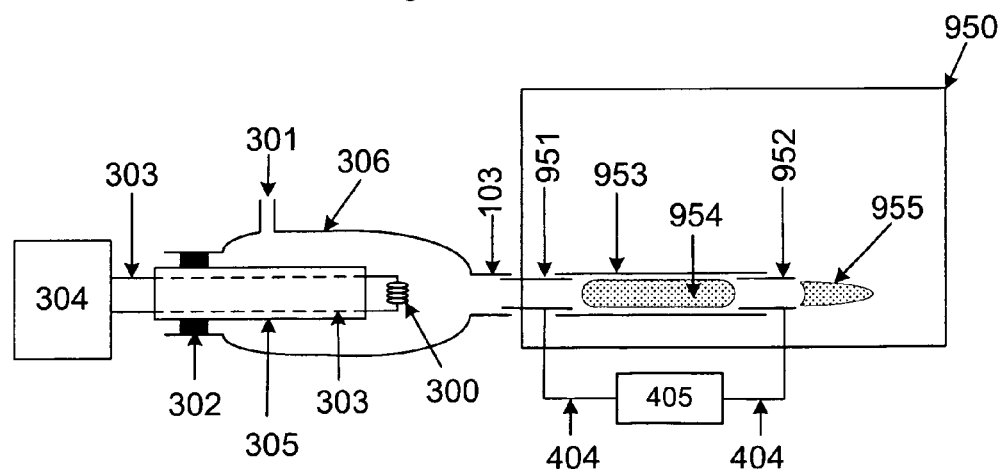
FIG. 9 is a schematic view of an exemplary embodiment of a miniaturized plasma device attached to (or integrated with) a miniaturized sample introduction device.

More specifically, for the embodiment shown in FIG. 9, for the miniaturized plasma device 950, a plasma 954 is formed between two tubular electrodes 951 and 952 in a glass or quartz tube (953). To reduce or eliminate transport losses, tubular electrode 951 may be affixed (using glass blowing techniques) to the exit port 103 of the vaporization chamber. Roughly and in all cases described in FIGS. 10-12, a mini-ITV is used when the diameter of the tubular electrodes is a few mm and a micro-ITV is utilized when the diameter is in the sub-mm range. Depending on carrier-gas (e.g., He, Ar) and carrier-gas 301 flow-rate, gas pressure and electrical power levels applied to the miniaturized plasma device 950 from the power supply 405, the plasma forming inside the glass or quartz tube 953 may also extend outside of it to the tube 952. This enables a multitude of optical plasma measurement schemes to be used as will be discussed in the section on signal measurement. The embodiments shown in FIGS. 10-12 have been devised to eliminate the possibility of analytes adhering (and possibly accumulating) in the front surfaces of electrodes 951 and 952. Those skilled in the art will recognize that glass-to-metal connections may be made so that the inner diameter of the outlet tube 103 of the vaporization chamber 306 will be the same as that of tubular electrodes 951 and 952 and of the glass or quartz tube 953. Although useful, such connections are costly due to extensive glass-blowing.

Figure 10:
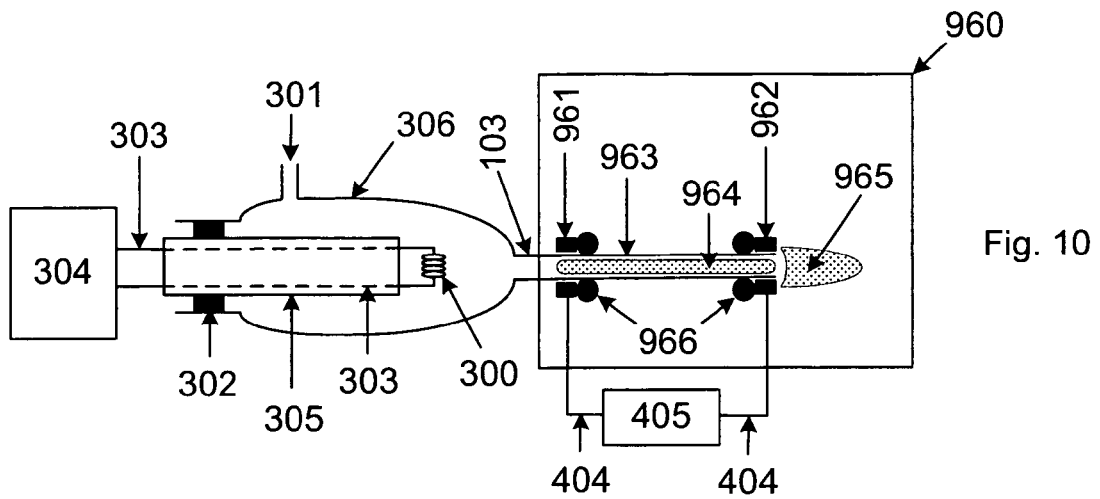
FIG. 10 is a schematic view of another exemplary embodiment of a miniaturized plasma device attached to (or integrated with) a miniaturized sample introduction device.
Figure 11:
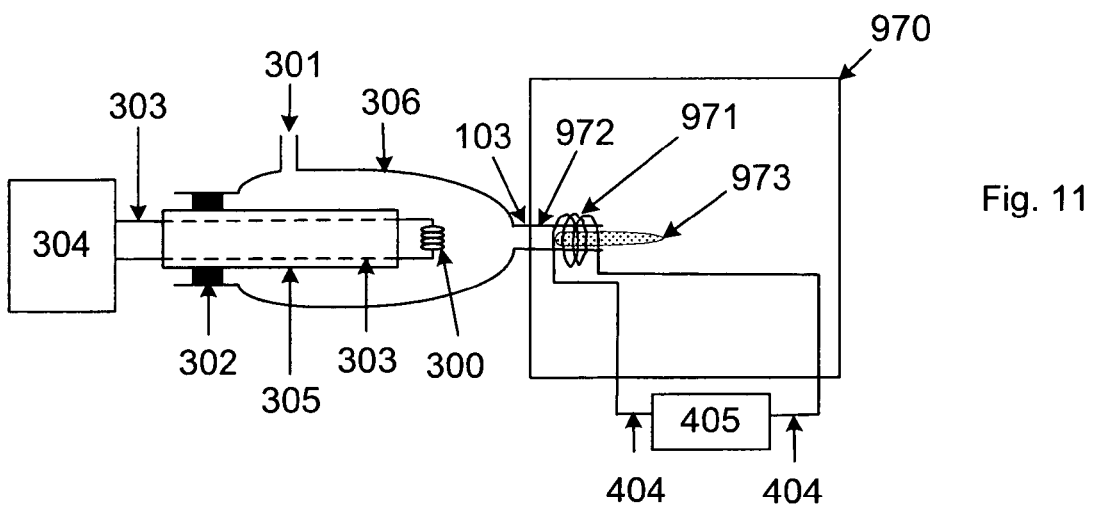
FIG. 11 is a schematic view of another exemplary embodiment of a miniaturized plasma device attached to (or integrated with) a miniaturized sample introduction device.
Figure 12:
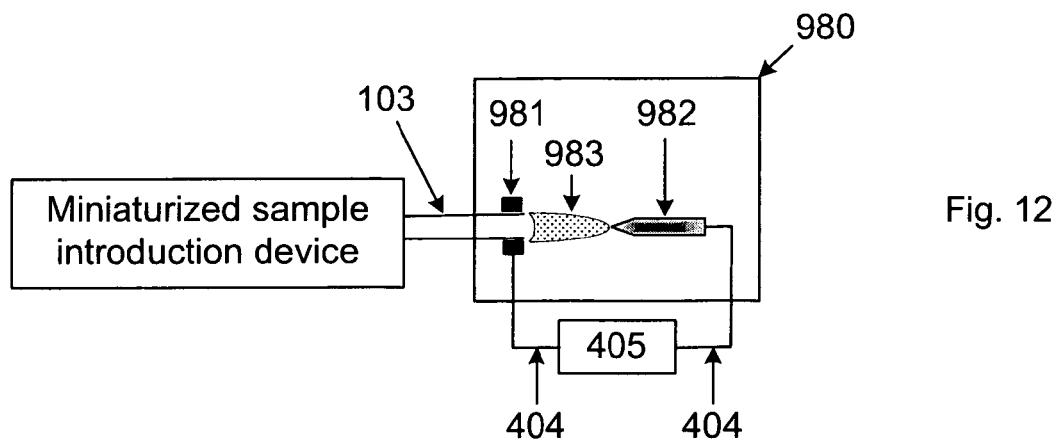
FIG. 12 is a schematic view of another exemplary embodiment of a miniaturized plasma device attached to (or integrated with) a miniaturized sample introduction device.

Cheaper and easier to make embodiments are shown in FIGS. 10-12. In FIG. 10, for example, a miniaturized plasma device 960 consists of tubular electrodes 961 and 962 (about 1 mm wide, 10-50 mm apart) placed outside an elongated outlet tube 103 of the vaporization chamber 306. The portion 963 of the elongated outlet tube 103 which is a glass or quartz tube, and is in between the electrode 961, 962 acts as a microplasma chamber. To avoid arcing between the electrodes 961 and 962, o-rings (not shown) are placed between the electrodes 961 and 962. As before, plasma 964 forms inside the tube 963, and depending on operating conditions, the plasma 964 also extends outside of the tube 963.

Another alternative embodiment is shown in FIG. 11. In this case, miniaturized plasma device 970 forms on glass or quartz tube 972 and electrical power from power supply 405 is transferred using cables 404 and a coil 971. Due to space limitations, plasma emission can only be observed when the plasma 973 is formed outside of the tube 972. An antenna may also be used in lieu of a coil, thus facilitating optical emission measurements through tube 972.

Another alternative embodiment, shown in FIG. 12, involves a miniaturized plasma device 980 in which the plasma 983 is formed between a tubular electrode 981 (about 1 mm wide) and a needle electrode 982. Such a miniaturized plasma device is useful when analytes with a high organic content are introduced, for example, such as those from a micro- or nano-high performance liquid chromatography (micro- or nano-HPLC) apparatus or from a gas chromatography (GC) apparatus. Oxygen from the atmosphere (or use of air as the plasma gas) facilitates combustion of organics, thus eliminating carbon deposits.

The embodiments illustrated in FIGS. 9-12, have been done so for exemplary purposes and should not be construed to limit the flexibility and versatility of the miniaturized plasma devices of the invention. Those skilled in the art will recognize that miniaturized plasma devices can be made using a variety of electrode configurations and such configurations are within the scope of the present invention.

Figure 13:
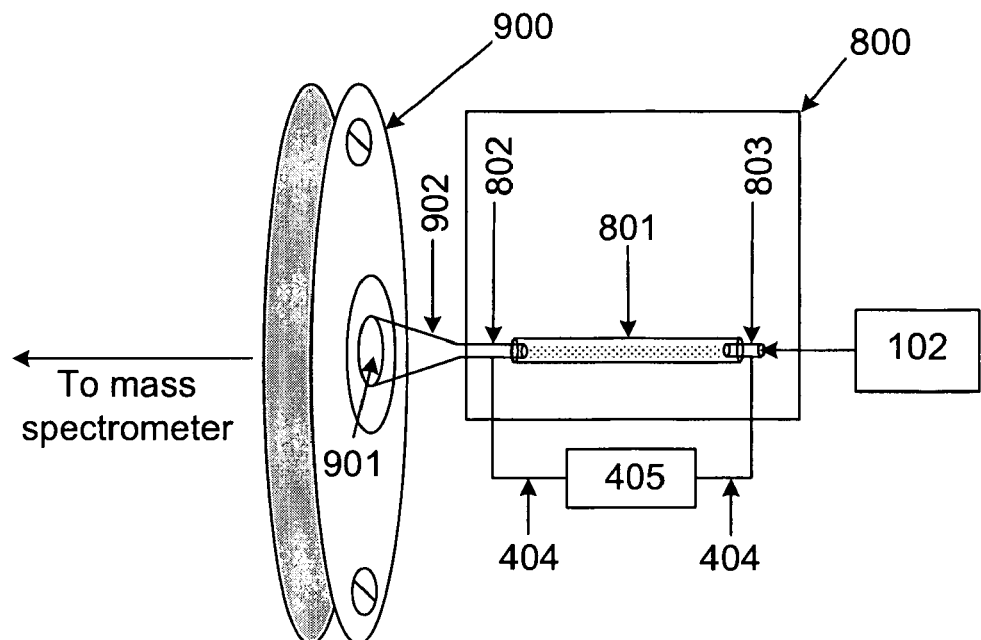
FIG. 13 is a schematic view of an exemplary embodiment of a miniaturized plasma device attached to a mass spectrometry device for ion measurements in accordance with the invention.

Referring now to FIG. 13, shown therein is a schematic view of an exemplary embodiment of the miniaturized tubular plasma device 800 and the sample introduction device 102 attached to a mass spectrometry device 900 for performing ion measurements. The inner diameter of the tubular electrodes 802 and 803 may be varied between 500 µm and 950 µm and the distance between the electrodes 802 and 803 may be varied between 5 and 50 mm, for example. The mass spectrometer 900 may be a quadrupole-based mass spectrometer, a time-of-flight mass spectrometer, a high-resolution mass spectrometer or an ion trap. A quadrupole-based mass spectrometer was used and the tubular geometry miniaturized plasma device 800 was soldered onto the sampling cone 901 of the mass spectrometer interface 900 using a tapered copper tube 902. Although not shown, a straight tube has also been used.

By using a longer length for the tube 801, improvements were seen in the measurements obtained by the mass spectrometer. However, as the length of the tube was increased, the start up voltage that was required to initiate the plasma discharge also increased.

Figure 14:
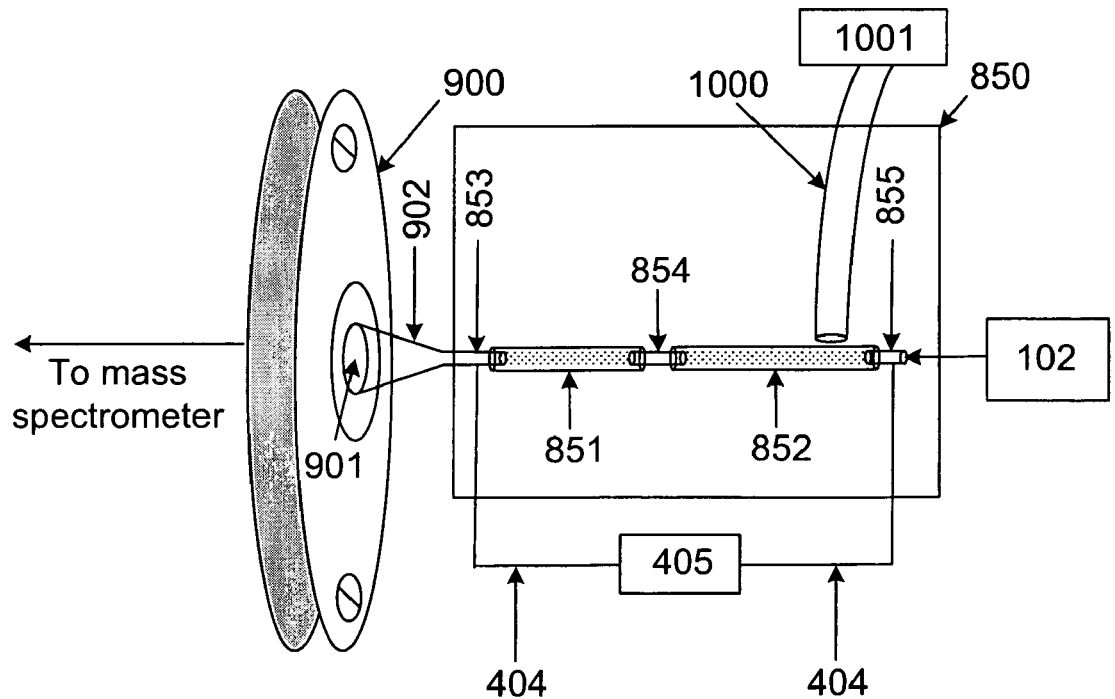
FIG. 14 is a schematic view of an exemplary embodiment of a tandem-source miniaturized plasma device attached to a mass spectrometer for ion measurements in accordance with the invention.

Referring now to FIG. 14, shown therein is a schematic view of an exemplary embodiment of a tandem-source miniaturized plasma device 850 attached to the mass spectrometer 900 for obtaining ion measurements in accordance with the invention. Although multiple tube-electrode segments may be used, the tandem-source miniaturized plasma device 850 includes a first tube or plasma chamber 851 and a second tube 852. The device 850 further includes three electrodes 853, 854 and 855 with apertures for allowing the sample to pass through. In some cases, middle electrode 854 may simply be a metallic tube that is not connected to the power supply 405. It can be considered to be a floating electrode and assumes the potential dictated by the voltage applied between electrodes 853 and 855. The electrode 855 acts as an input conduit to receive the sample from the sample introduction device 102. The electrode 854 acts as a conduit between the two tubes 851 and 852 and the electrode 853 provides an output conduit to the mass spectrometer 900. Electrical contacts 404 connect the two exterior electrodes 853 and 855 to the power supply 405. It should be noted that in other embodiments, two (or more) planar devices with collinear input and output conduits may be used rather than using two tubular plasma devices. Elements 1000 and 1001 are a fiber optic cable and an optical spectrometer respectively. These elements are optional and are discussed in more detail below.

In use, a few μL of sample is deposited on the coiled filament 300 of miniaturized sample introduction 102. The sample is dried by applying low electrical power from power supply 304 to the coiled filament 300 (via cables 303), causing a dried solution residue to remain on the coil filament. Electrical power from power supply 405 is applied (via cables 404) to the tandem source 850 and the plasma self-ignites. Higher electrical power is applied to the coiled filament 300, thus rapidly vaporizing the solution residue that remained on the coil. Rapid vaporization generates a plug of sample vapor and the vaporized sample is introduced into tube 852. The plug of sample vapor crosses through electrode 854 into tube 851. The plug of sample vapor is ionized and the plasma gas and the sample ions are then introduced (via tube 902) into the sampling orifice of the sampling cone 901. The vacuum of the mass spectrometer 900 ensures that ions are introduced into the mass spectrometer 900. Ions entering the mass spectrometer 900 are mass analyzed according to their m/z and are measured using a detector (not shown). The operation of mass spectrometers is well known to those skilled in the art. The duration of the plug of sample gas (and as a consequence of the ion signals) is about 1 second or less (depending on vaporization power applied to the coiled filament 300).

The inventor has found that the tandem miniature plasma source device 850 does not require a high start up voltage. In fact, start up voltages similar to the miniature plasma source 800 can be used. In addition, the tandem-source approach increases the sample residence time in the plasma and this has been found to improve analytical performance. The tubular miniature plasma source device geometry and in particular the tandem-source can also find use as a replacement of the power- and gas-consuming large-scale ICP, thus resulting in significant reductions in operating costs. Alternatively, a miniature plasma source device can serve as an ion source for miniaturized mass spectrometers that are beginning to become commercially available, thus facilitating portability. Alternatively, they may be used as portable total ion current detectors. Such detectors will be described next.

Figure 15:
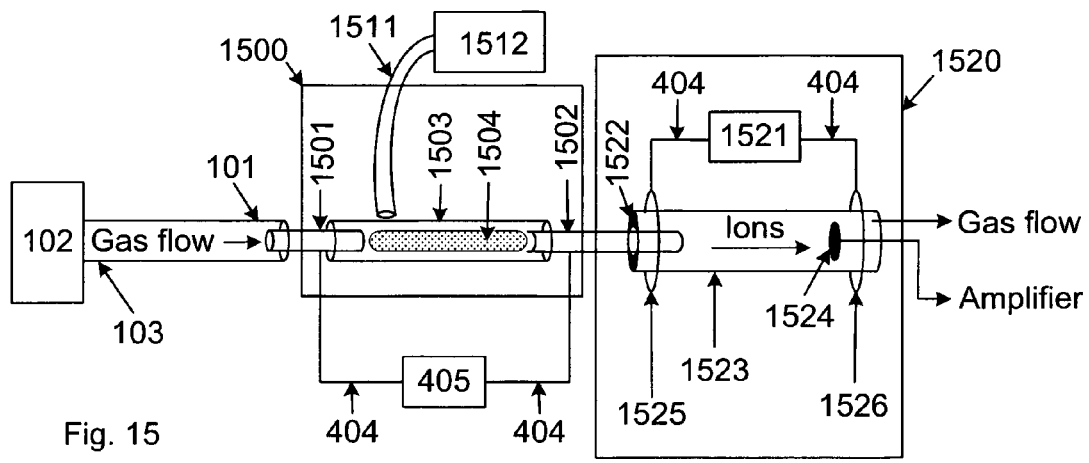
FIG. 15 is a schematic view of an exemplary embodiment of a tubular miniaturized plasma device attached to a tubular atmospheric pressure total ion current detector (abbreviated as tubular APTIC detector)

An embodiment of a portable, tubular-geometry atmospheric pressure total ion current detector is shown in FIG. 15. In use, a dried solution residue (as described above) from a miniaturized sample introduction system 102 is vaporized and is introduced into a miniaturized plasma device 1500 through tubular electrode 1501. The plasma 1504 is formed between tubular electrodes 1501 and 1502 (with an inner diameter of 950 μm and positioned 20 mm apart, for example) and is contained within tube 1503. Sample ions formed in plasma 1504 exit through tubular electrode 1502 and enter a 2 mm (inner diameter), 5 cm long glass tube 1523. The seal 1522 ensures air and atmospheric contaminants do not enter the tube 1523. Thus ions only experience the environment of the inert gas-flow (e.g., Ar, He). Under the influence of the gas flow, ions travel to a Faraday plate detector 1524 and are detected using a current amplifier (such as the one available from Stanford Research Systems Inc., model 570). A voltage (typically 500 V dc) is applied between the two ring electrodes 1525 and 1526 (which are made out of 2 mm thick washers). The voltage helps focus the ions in the center of the tube 1523, thus reducing their loss to the walls of the tube 1523. The total ion current provides rapid information. For example, a dried solution residue is vaporized by applying relatively low electrical power levels from the power supply 304 to the coil filament 300 (for example, translating to coil temperatures below about 300° C.). The vaporized sample is then introduced into the miniature plasma source 1500. Such temperatures are sufficient to vaporize, for example, semi-volatile organic compounds that may be present in the dry sample residue. Absence of an ion current (e.g., background levels) at the detector 1524 indicates absence of such compounds in the dry residue, therefore the sample under consideration does not need to be further analyzed in the laboratory. Subsequent application of higher vaporization potentials to the coil filament 300 (for instance, to provide coil temperatures of about 1600° C.) will vaporize environmentally important elements, such as, Pb, Cd and Zn. Absence of an ion current (e.g., background levels) at the detector 1524 also indicates that these elements are not present in the dry residue; therefore the sample under consideration does not need to be analyzed in the laboratory for these elements. Such rapid screening is important in environmental monitoring of water samples, for instance. The rapid screening method outlined above can be used in the field so that samples that are considered "suspect" can be sent to the lab for detailed analysis. Thus, considerable costs savings can be obtained as the majority of samples used in environmental monitoring are "non suspect" (but must still be sampled in the field and analyzed in the lab often using costly analytical instrumentation and methodology).

Figure 16:
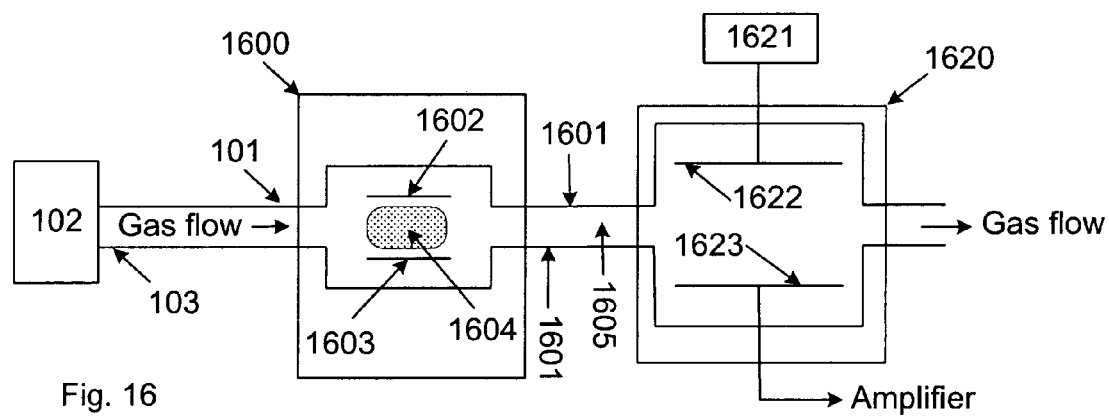
FIG. 16 is a schematic view of an exemplary embodiment of a planar miniaturized plasma device attached to a planar atmospheric pressure total ion current detector (abbreviated as planar APTIC detector)
Figure 17:
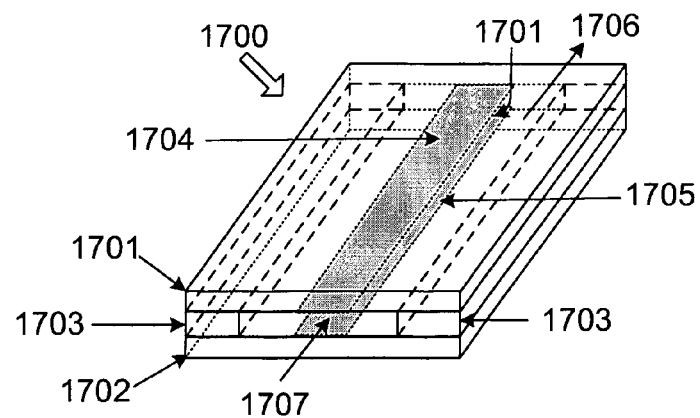
FIG. 17 is an isometric view of an exemplary embodiment of an alternative planar microplasma device in accordance with the invention.

An alternative embodiment of a portable, planar-geometry atmospheric pressure total ion current detector is shown in FIG. 15. For example, in the miniature plasma device 1600 of FIG. 16, the plasma 1604 is formed between two planar metal electrodes 1602 and 1603 that oppose each other. The electrodes are typically 2 mm wide, 10 mm long with an inner electrode distance preferably 1 mm (or less), for example. A vaporized sample from the miniature sample introduction device 102 is carried by the gas-flow into the miniature plasma device 1600 where it is ionized. Ions generated in the miniature plasma device 1600 are carried through channel 1601 into a planar atmospheric pressure total ion current detector 1620. The planar APTIC detector 1620 may be enclosed in a glass structure and includes two metal electrodes1 622 and 1623 opposing each other. The electrodes are typically 4 mm wide, 15 mm long and have an inner electrode distance of about 5 mm. Electrode 1622 is connected to an electrical, dc power supply 1621 that applies voltages in the range of 5 to 15 V or −5 to −15 V. Ions deflected due to the voltages applied to the electrode 1622 are collected by the electrode 1623 and the current is amplified using, for example a commercially available current-to-voltage converter (such as model 570, Stanford Research Systems, Inc.). The planar APTIC detector 1620 can be used as described above for the tubular APTIC detector 1520. Instead of using metal electrodes, the miniature plasma device 1600 can be microfabricated. An exemplary embodiment of such a microfabricated device is shown in FIG. 17. On the top side of a glass or quartz wafers 1701 and 1702 metal electrodes 1704 and 1705 are sputter deposited. Depending on intended use, and to reduce the potential for oxidation, a thin insulation layer (<1 μm) is thermally grown. Two spacers are placed on top of the bottom wafer 1702 and the top wafer 1701 is turned over so that the two electrodes 1704, 1705 are facing each other. The opening between spacers 1703 and the top and bottom wafers 1701 and 1702 form a rectangular channel, or microplasma chamber, with inlet 1707. The plasma 1701 is formed between electrodes 1704 and 1705. Ions formed in the plasma exit through outlet 1706 to enter the planar APTIC detector 1620. The detector 1620 can also be microfabricated. Exemplary dimensions for the miniature plasma device and the miniature, planar APTIC detector are the same as those mentioned above.

From the foregoing discussion, those skilled in the art will recognize that the approach disclosed in this invention offers a great deal of flexibility in selection of geometries, materials and fabrication methods, and all such geometries, materials and methods are within the scope of the invention.

Signal Measurement

Figure 18:
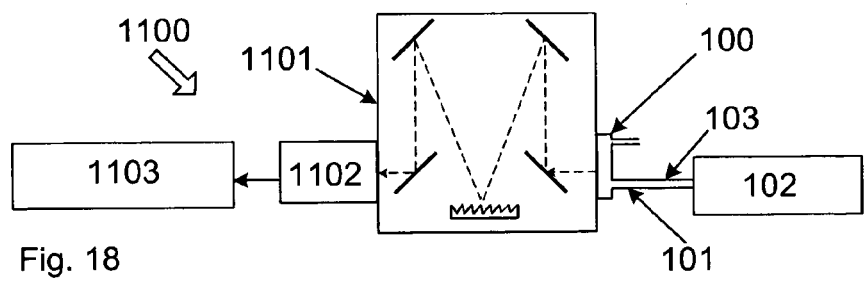
FIG. 18 is a schematic view of an exemplary embodiment of a measurement device including a miniaturized plasma source with a miniaturized sample introduction interface and being configured for obtaining emission measurements by optical spectrometry in accordance with the invention.

In addition to detection of ions by mass spectrometry (as discussed in conjunction with FIGS. 13 and 14), the miniaturized sources can be used for detection of photons as well. Referring now to FIG. 18, shown therein is a schematic view of an exemplary embodiment of a measurement device 1100 including the miniaturized plasma source 100 with the miniaturized sample introduction interface 102 and being configured for obtaining emission measurements by optical spectrometry in accordance with the invention. In this case, the miniaturized plasma source 100 may be attached to the side of a monochromator 1101 equipped with a photomultiplier tube detector 1102 and appropriate analysis electronics 1103 for measuring transient signals. An implementation of such analysis electronics has been disclosed in U.S. Pat. No. 6,184,982 which is hereby incorporated by reference. Those skilled in the art will recognize that improved analytical performance can be obtained by using one or more optical-lenses to couple light emission from the miniaturized source 102 to the monochromator 1101. The optical lenses are located between the miniaturized plasma device 100 and the entrance slit of the monochromator 1101. Further, the monochromator or single channel spectrometer 1101 can be replaced either by a PMT-based filter photometer or by a multi-channel PMT-based direct reading spectrometer that can provide simultaneous detection capabilities.

Alternatively, the monochromator 1101 can be replaced by a portable, palm-size spectrometer with linear array detectors, of the type manufactured either by Ocean Optics, Danedin, Fla., USA or by StellarNet Inc. of Oldsmar, Fla., USA thus facilitating portability. An example of this is shown in FIG. 14 in which a fiber optic cable 1000 couples light emission from the miniaturized plasma sources 851 and 852 to an optical spectrometer 1001 such as the one manufactured by Ocean Optics. Accordingly, in the embodiment shown in FIG. 14, both photon and ion information about a sample is obtained. If a conventional mass spectrometer is used, then the system shown in FIG. 14 is not portable (due to the size and weight of the mass spectrometer). However, the system may still find significant applicability in the laboratory, for instance, as a replacement for the traditional ICP source since state-of-the-art ICP-MS systems are expensive to purchase and operate due to large gas consumption. Replacing the ICP source with the one shown, for example in FIG. 14, reduces initial purchasing costs. Further, the low gas consumption of miniaturized plasma devices reduces operating costs. A reduction of operating costs translates to a reduction of the cost-per-analysis. Alternatively, a portable system to be used for rapid screening of environmental samples has been developed around the atmospheric pressure total ion current detector with an exemplary embodiment shown in FIG. 15.

There are additional benefits that arise from the optical coupling of the analysis devices shown in FIGS. 13 and 14. For instance, traditional ICP-MS systems equipped with pneumatic nebulization sample introduction interfaces suffer from spectral interference effects arising mainly from the water solvent. Further, because the ICP operates in the open atmosphere, molecular oxides formed due to air entrainment by the ICP are also a major source of spectral interference. However, in the approach shown in FIGS. 13 and 14, a miniaturized sample introduction system 102 delivers dry samples to be turned into a plasma, thus there are no molecular oxides from the water. In addition, since the miniaturized plasma source 100 operates in an enclosed environment, there is no air entrainment. Thus, interferences from molecular oxide ions is reduced or eliminated.

Figure 19:
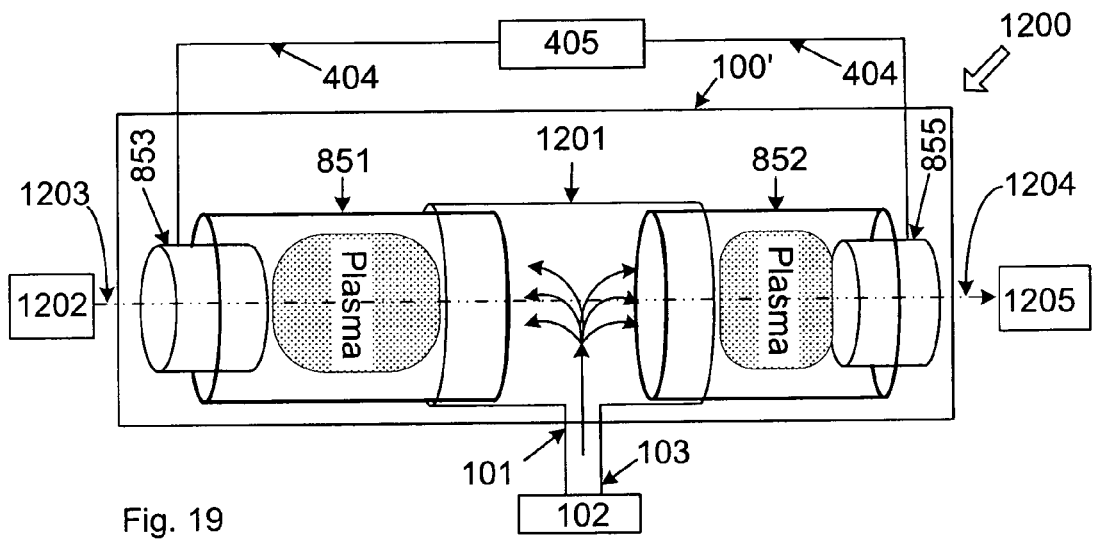
FIG. 19 is a schematic view of an exemplary embodiment of a measurement device including a miniaturized plasma source with a miniaturized sample introduction interface and being configured for obtaining absorption measurements in accordance with the invention.

In addition to optical emission, miniaturized plasma devices can be used for absorption measurements. Referring now to FIG. 19, shown therein is a schematic view of an exemplary embodiment of a measurement device 1200 including the miniaturized plasma source 100' with a miniaturized sample introduction interface 102 and being configured for obtaining absorption measurements in accordance with the invention. The miniaturized plasma source 100' is a slightly modified version of the tandem-source miniaturized plasma device 850. The miniaturized plasma source 100' includes the tubes 851 and 852 along with the electrodes 853 and 855. However, a modified electrode 1201 is included which has three apertures; two of the apertures serve as entries/exits for the tubes 851 and 852 while the other aperture is connected to the outlet 103 of the sample introduction device 102. A dual plasma is formed between electrodes 853 and 1202 and 1202 and 855. A spectral lamp 1202 (such as a commercially available hollow cathode lamp, Varian, Melbourne, Australia) emits light 1203 at the wavelength of interest. Analyte vapor introduced into the plasma from the sample introduction device 102 absorbs light 1203 emitted from the spectral lamp 1202. The absorbed light 1204 is measured using an appropriate spectrometer and analysis electronics 1205. This occurs for both ends of the tubes 851 and 852 that are opposite the end to which the electrode 1201 is connected. In addition to reducing plasma start-up voltage, the three electrode configuration 853, 1201 and 855 effectively extends the length of the miniaturized plasma source, thus increasing absorption path length and residence time of analytes in the plasma. This results in improved analytical performance characteristics.

Figure 20:
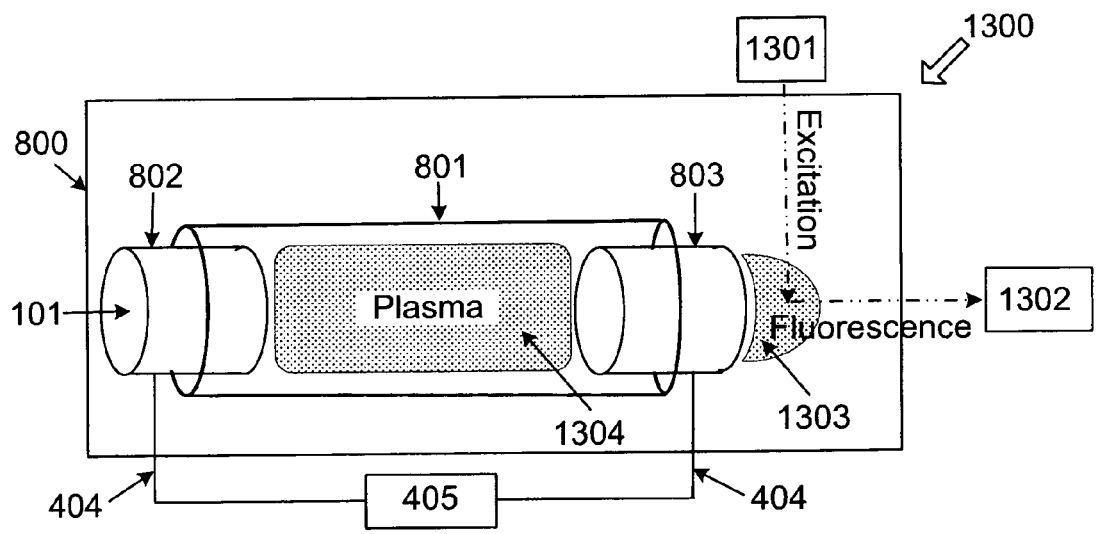
FIG. 20 is a schematic view of an exemplary embodiment of a measurement device including a miniaturized plasma source which receives a sample from the miniaturized sample introduction interface (not shown) and is configured for obtaining fluorescence measurements in accordance with the invention.

Alternatively, fluorescence rather than absorption can be measured. Referring now to FIG. 20, shown therein is a schematic view of an exemplary embodiment of a measurement device 1300 including the miniaturized plasma source 800 which receives a sample from the miniaturized sample introduction interface 102 (not shown). The measurement device 1300 is configured for obtaining fluorescence measurements in accordance with the invention. Fluorescence is preferably measured in the part of the plasma 1303 that extends outside of the miniaturized plasma chamber 1304. The inventor found that the plasma extends outside of the plasma chamber 1304 when the tube 801 was longer than about 7 cm (i.e. the distance between the electrodes 802 and 803) and when the flow-rate was between 200 and 300 mL/min. Although fluorescence can be measured though the plasma chamber 1304, measurement outside of the plasma chamber 1304 is preferred because such measurements eliminate background fluorescence from the walls of the tube 801. The excitation light source 1301 can be a (pulsed) commercially-available hollow cathode lamp or, for some embodiments depending on wavelength, a laser such as a semiconductor laser. The fluorescence signal may be measured using an appropriate spectrometer and analysis electronics 1302.

The signal measurement modes described above have been included to illustrate that the invention is versatile in its signal measurement modes as well. As demonstrated, emission, absorption, fluorescence and mass spectrometry can be employed without the need to modify either of the miniaturized devices and without deviation from the scope of the invention. It should be understood that although tubular microplasma source devices were shown in the measurement devices of FIGS. 13 and 14 and FIGS. 19 and 20, planar microplasma source devices may also be used in certain cases. Furthermore, it should be understood that amplifiers may be used along with the data acquisition and signal processing circuitry that is used to process the measured results for the measurement devices shown in FIGS. 18-20.

EXAMPLE APPLICATIONS

To illustrate analytical performance characteristics (with particular emphasis on detection limits), selected examples will be described. Unless otherwise stated, the signals were obtained using a measurement device as configured in FIG. 18 in which the spectral bandpass of the monochromator 1101 was increased to match that of a low resolution, portable, fiber-optically coupled spectrometer, such as the diode-array based StellarNet spectrometer mentioned above.

Example 1

Figure 21:
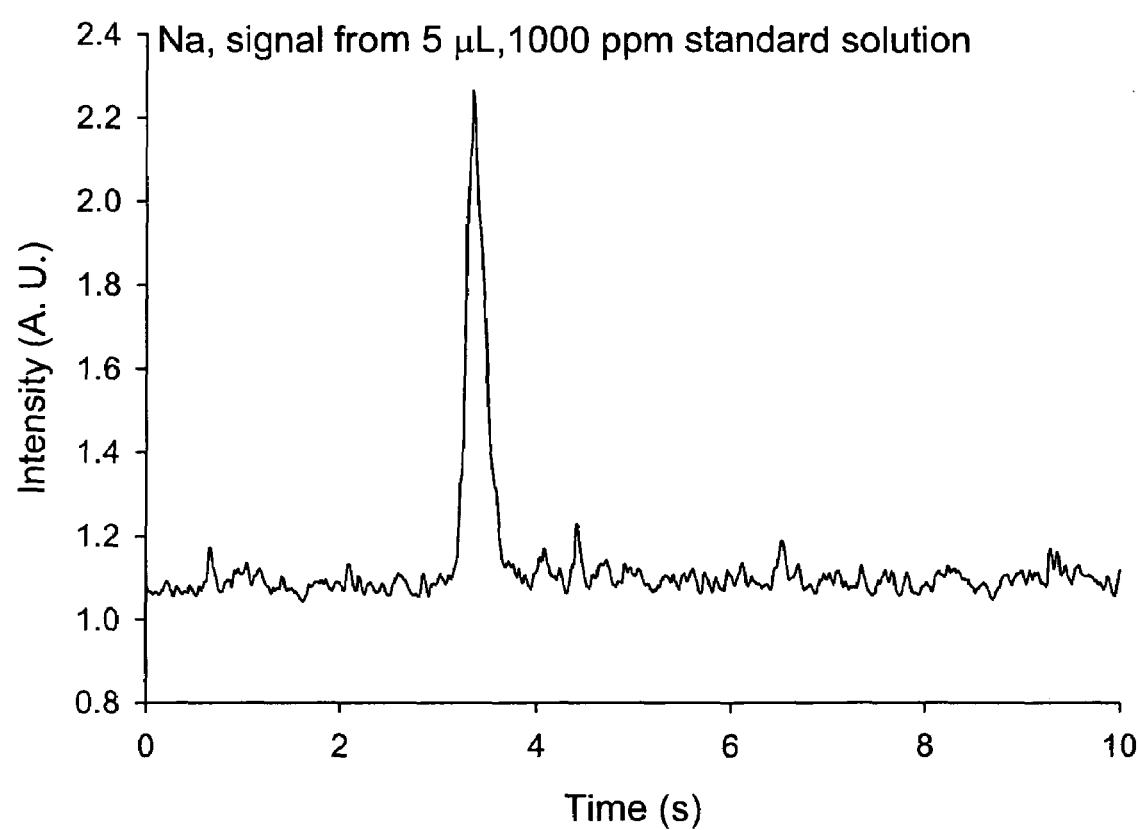
FIG. 21 is a graph showing a transient emission signal obtained from analysis of a 1000 ppm Na analyte obtained using a 5 µL volume of standard solution with a measurement device having a DC operated planar-geometry microplasma device (of the type shown in FIG. 4 for example) and being configured for AES measurements (as shown in FIG. 18 for example)

In this example, the planar microplasma source device 400 shown in FIG. 4 was used. The microplasma was generated by applying a potential difference of 3500 V DC across the electrodes 403. Both the miniaturized sample introduction device 102 and the microplasma source device 100 were operated as described previously. Briefly, 5 μL of a 1000 ppm standard stock solution of Na was pipetted onto the coiled filament 300 of the mini-ITV (described in FIG. 3). The solution was dried, the microplasma device 400 was turned on, the dried solution residue that remained on the coil 300 was vaporized and the 586 nm spectral line of Na was monitored in the time-domain. An example of a transient signal so obtained is shown in FIG. 21. Calibration curves were linear, detection limits were in the 100's of ppb and precision was at about 30%. In particular, device lifetime was a key concern since the microplasma source devices were unusable after about two hours of operation. The short lifetime was attributed to sputtering due to DC operation. When DC voltage was replaced by AC voltage, the lifetime of the microplasma source device 400 increased to a couple of days and precision was at acceptable (10%) levels.

Figure 22:
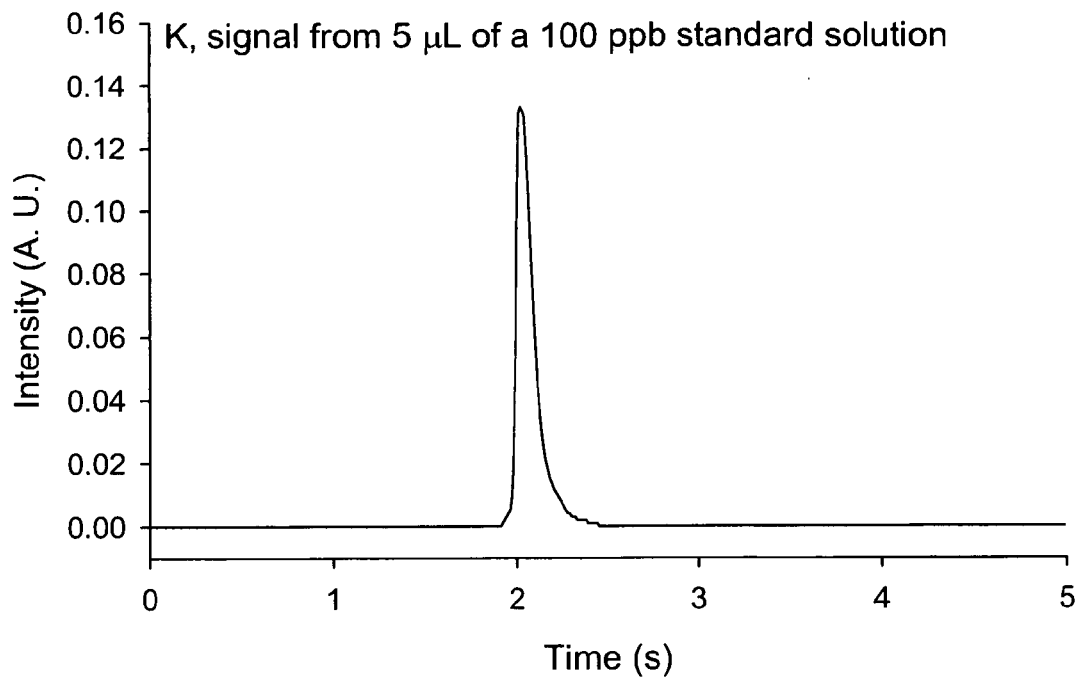
FIG. 22 is a graph showing a transient emission signal for a 100 ppb K analyte obtained from analysis of a 5 µL volume of diluted standard solution of K with a measurement device having a DC operated planar-geometry microplasma device (of the type shown in FIG. 4 for example) and being configured for AES measurements (as shown in FIG. 18 for example)
Figure 23:
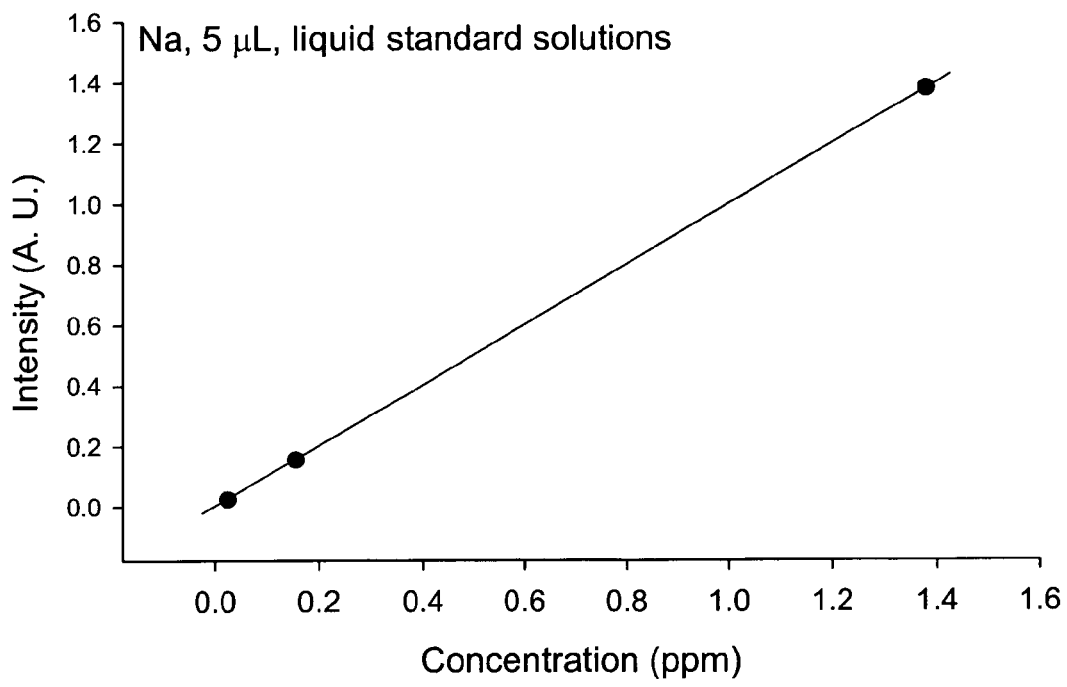
FIG. 23 is a calibration curve for Na obtained from analysis of a 5 µL volume of diluted standard solutions of Na with a measurement device having an AC operated planar-geometry microplasma device (of the type shown in FIG. 7 for example) and being configured for AES measurements (as shown in FIG. 18 for example)
Figure 24:
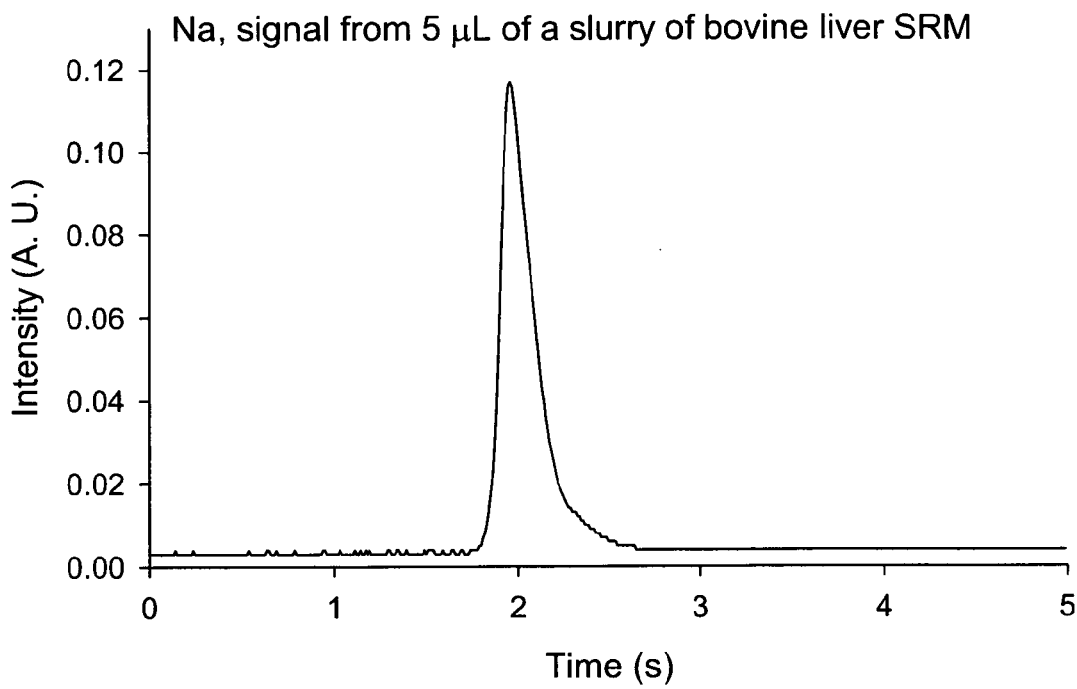
FIG. 24 is a graph of a transient emission signal for Na obtained from analysis of a 5 µL volume of a slurry of powdered bovine liver SRM (i.e., a solid sample) with a measurement device having an AC operated planar-geometry microplasma device (of the type shown in FIG. 7 for example) and being configured for AES measurements (as shown in FIG. 18 for example)
Figure 25:
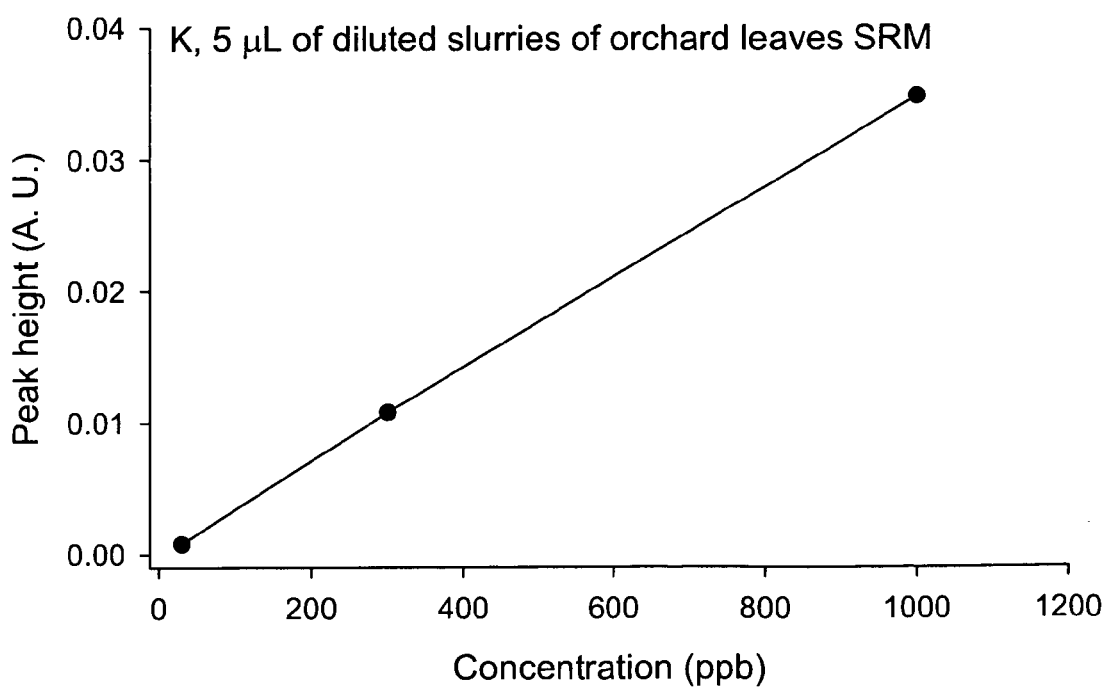
FIG. 25 is a graph of a calibration curve for K obtained from analysis of a 5 µL volume of slurries of powdered orchard leave SRM (i.e., a solid sample) with a measurement device having an AC operated planar-geometry microplasma device (of the type shown in FIG. 7 for example) and being configured for AES measurements (as shown in FIG. 18 for example)

Detection limits improved when a device geometry of the type shown in FIG. 7 was used in which the electrodes were made from Mo strips. In addition, device lifetime increased to several weeks. In addition to the desirable properties of Mo, the increase in device lifetime was attributed to reduced sputtering of the electrode material (due to AC operation) and to the lack of thermal stress on the electrodes (due to the short time that the plasma device was turned on). There was also a lack of material from the Mo electrodes that entered the plasma so that there was reduced contamination and spectral interference effects. This was confirmed experimentally using optical emission measurements and the measurement set up shown in FIG. 18. The lack of signal obtained by observing the most intense Mo spectral line proved that contamination from the Mo electrode was not a problem. With device lifetime addressed, analytical signals were obtained using the procedure described above. An example of a measurement is shown in FIG. 22 which shows a graph of a transient emission signal for a 100 ppb K analyte obtained from analysis of a 5 μL volume of diluted standard solution of K with an AC operated planar-geometry microplasma device (of the type shown in FIG. 7 for example) configured for AES measurements (as shown in FIG. 18 for example). Although a direct comparison is not possible, from the signals shown in FIGS. 21 and 22 it can be concluded that device geometry and AC operation improved signal intensities significantly. For instance, calibration curves (see FIG. 23) obtained using 5 μL of diluted standard stock solutions of Na were linear down to 30 ppb level. In addition, AC operation appears to have enabled better power coupling between the power supply and the miniaturized plasma source device. The improvement was also attributed to the fact the plasma filled the entire plasma chamber 705 thus facilitating sample-plasma interactions. The miniaturized plasma source devices were tested with solid samples by preparing water-based slurries of powdered Standard Reference Materials (available from NIST, Gaithersburg, Md., USA) and by pipetting 5 μL of the slurry onto the coiled filament 300 of the mini-ITV sample introduction device. A sample pipetted on the coil 300 was subsequently processed (e.g., dried etc.) as previously described. Results are shown in FIGS. 24 and 25. Specifically, FIG. 24 shows a graph of a transient emission signal for Na obtained from analysis of a 5 μL volume of a slurry of powdered bovine liver SRM (i.e., a solid sample) with an AC operated planar-geometry microplasma device (of the type shown in FIG. 7 for example) configured for AES measurements (as shown in FIG. 18 for example). FIG. 25 shows a graph of a calibration curve for K obtained from analysis of a 5 μL volume of slurries of powdered orchard leave SRM (i.e., a solid sample) with an AC operated planar-geometry microplasma device (of the type shown in FIG. 7 for example) configured for AES measurements (as shown in FIG. 18 for example). Both of these figures clearly demonstrate that miniaturized plasma devices can be used with solid samples provided that an appropriate dry sample introduction system is used.

Figure 26:
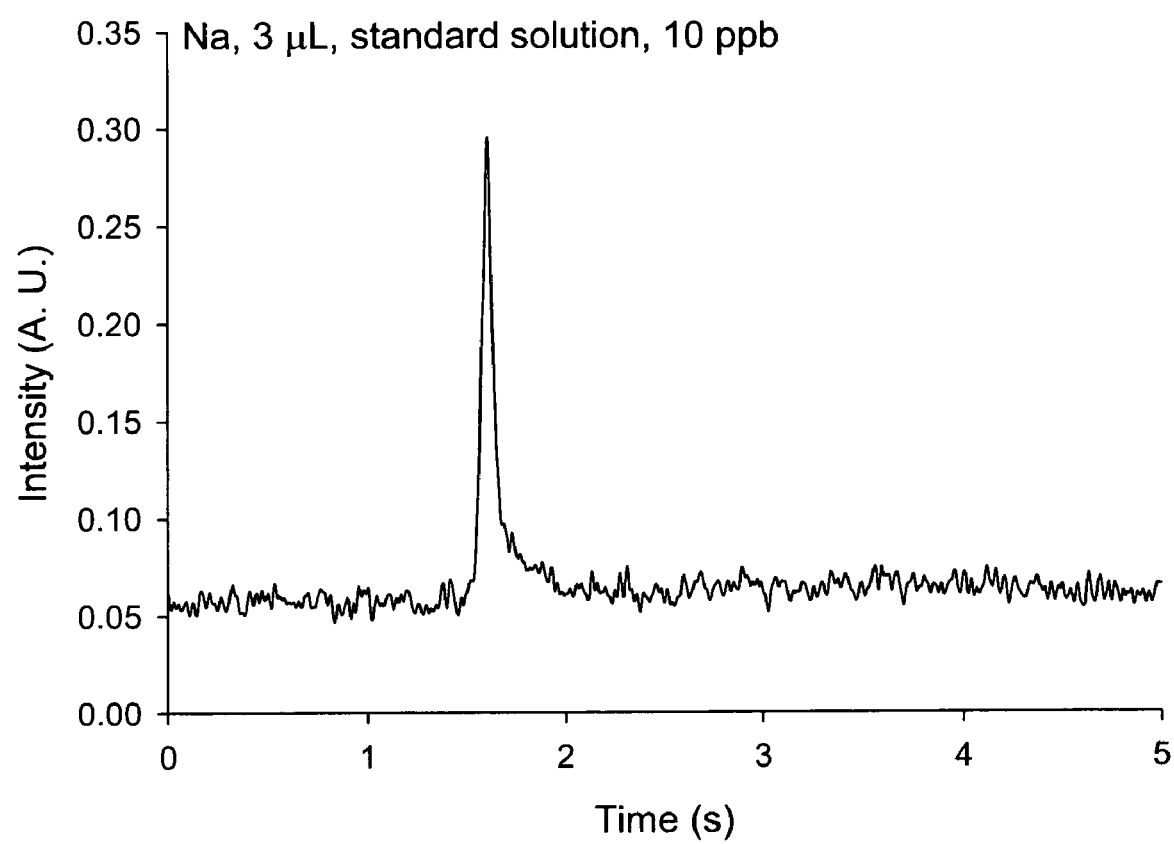
FIG. 26 is a graph of a transient emission signal for Na obtained from analysis of a 3 µL of a 10 ppb standard solution of Na with a measurement device having an AC operated, tubular-geometry miniaturized plasma device (of the type shown in FIG. 8 for example) being configured for AES measurement (as shown in FIG. 18 for example)

Testing was also conducted using the co-linear inlet-to-outlet tubular geometry of the type shown in FIG. 8 to determine whether detection limits from liquid samples can be further improved with this type of geometry. FIG. 26 shows a graph of a transient emission signal for Na obtained from analysis of a 3 μL of a 10 ppb standard solution of Na with an AC operated, tubular-geometry miniaturized plasma device (of the type shown in FIG. 8 for example) configured for AES measurement (as shown in FIG. 18 for example). There was an improvement in detection limits and it was attributed to enhanced transport efficiency from the sample introduction system to the microplasma source device. The detection limits were in the low hundreds of ppt-range (parts-per-trillion) or in the sub-pg (less than picogram) range when expressed in absolute units. Despite the small size, low power and gas consumption and use of a wide spectral bandpass for the microplasma source device 800, the detection limits confirm that miniaturized plasma source devices can perform equally as well as their large size counterparts.

Figure 27:
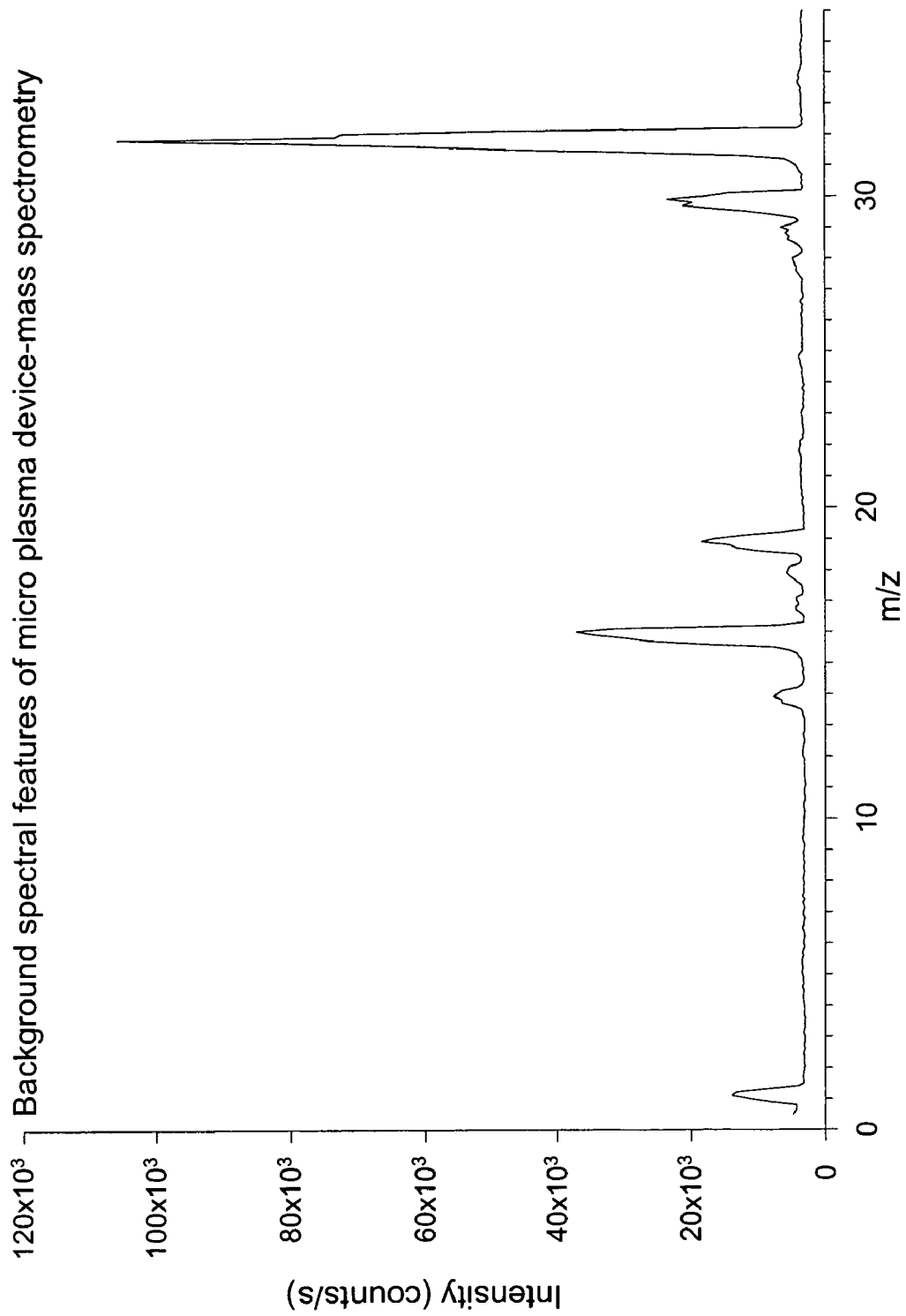
FIG. 27 is a graph showing MS background spectral features obtained using a tubular-geometry microplasma device configured in the measurement set up shown in FIG. 13.

It has been shown thus far that miniaturized plasma devices have sufficient energy density to excite analytes introduced into them provided that a dry sample introduction device is used. Would dry sample introduction coupled with the enclosed plasma geometry offer simplification of the background spectral features, thus potentially reducing spectral interference from molecular oxide ions in MS as described previously? This question was addressed using the geometry shown in FIG. 13. FIG. 27 is a graph showing MS background spectral features obtained using the tubular-geometry microplasma device configured with the mass spectrometer in the measurement set up shown in FIG. 13. Miniaturized plasma source device-MS background spectral features are shown in FIG. 27. The peak at a mass charge ratio (m/z) of 18 with an intensity of about 20,000 counts/s is due to water (originating from water in the Ar gas supply used for this work). By comparison, when an ICP is used with the same MS system utilizing a pneumatic nebulizer for sample introduction, the corresponding water peak has an intensity of more than 3,000,000 counts/s (the detector saturates at about 3 million counts). The spectral simplicity of the background spectral features means that spectral interferences from molecular oxide and hydroxide ions are significantly reduced with the miniaturized microplasma source devices of the invention. Furthermore, miniaturized plasma sources can be operated either at low electrical power levels (e.g., a few Watts or less) or at high electrical power levels (e.g., about 10 Watts). This way the properties (e.g., electron concentrations) of such plasma sources are easy to control. For instance, low electrical power can be used to provide fragmentation patterns from organics introduced into a miniaturized plasma source and high power levels (as defined above) to provide elemental composition. Thus some information on the identity of organic species that may be present in a sample can be obtained. This "tunable source" capability is not available in large-scale spectrochemical sources such as the ICP but is very easy to obtain using miniaturized plasma sources.

Figure 28:
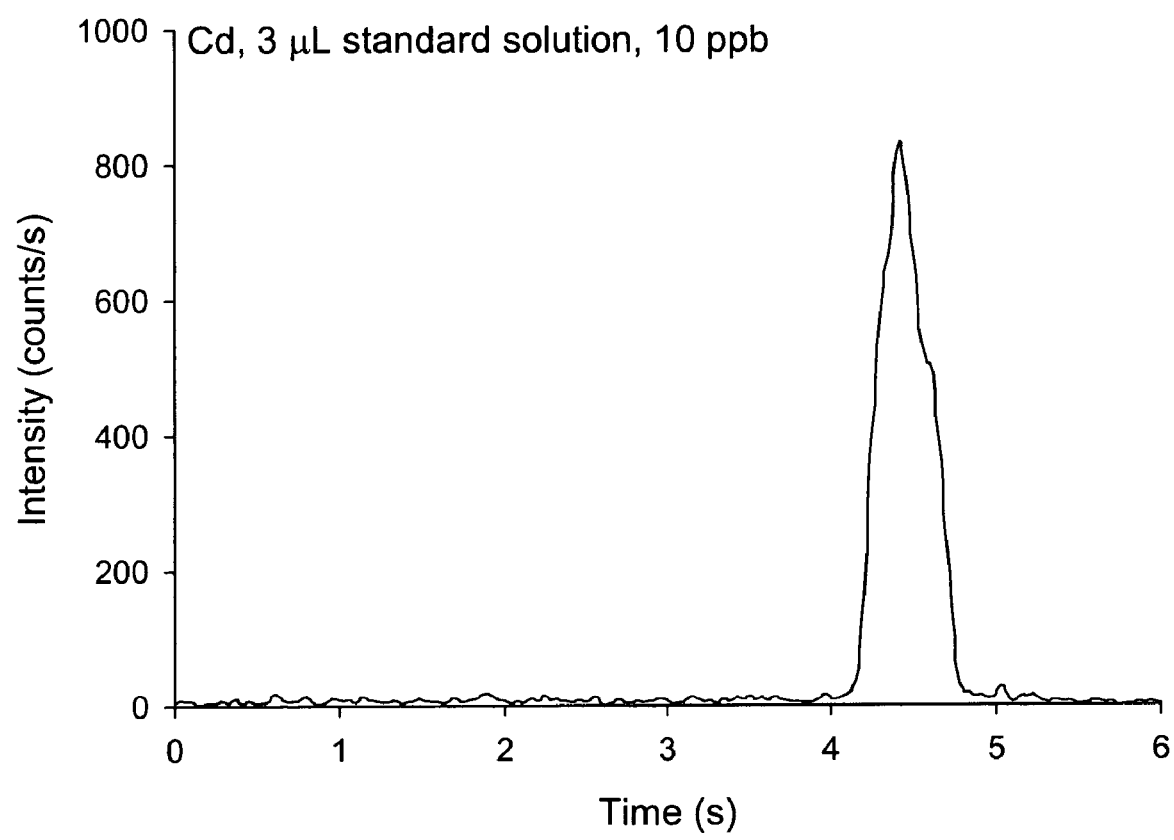
FIG. 28 is a graph of a transient signal obtained from analysis of a 3 µL of 10 ppb standard solution of Cd using a tandem-source miniaturized plasma device configured in the measurement set up shown in FIG. 14.

Do miniaturized plasma devices have sufficient energy density not only to excite analytes but also to ionize them? This question was addressed using the tandem-source geometry shown in FIG. 14 with an exemplary sample of 3 μL of a 10 ppb standard solution of Cd. The measurement results are shown in FIG. 28 and they indicate that the miniaturized plasma devices have sufficient energy density to ionize analytes introduced into them. This further proves that miniaturized plasma source devices can provide analytical performance comparable to that offered by large scale ICP sources. Because the MS results are independent of spectrometer resolution (all quadrupole-based ICP-MS systems have unit mass resolution), they provide a resolution-independent measure of analytical performance. Overall, the detection limits were in the sub-pg range (absolute) and the ppt range (expressed in relative concentration units). Such detection limits open up the possibility for obtaining viable analysis results from smaller amounts of samples (e.g., nano-size samples either ng or nL) containing relatively large concentrations of analytes. Accordingly, the miniaturized plasma source devices can offer an inexpensive and low-operating cost alternative to ICP for measurements by MS.

Figure 29:
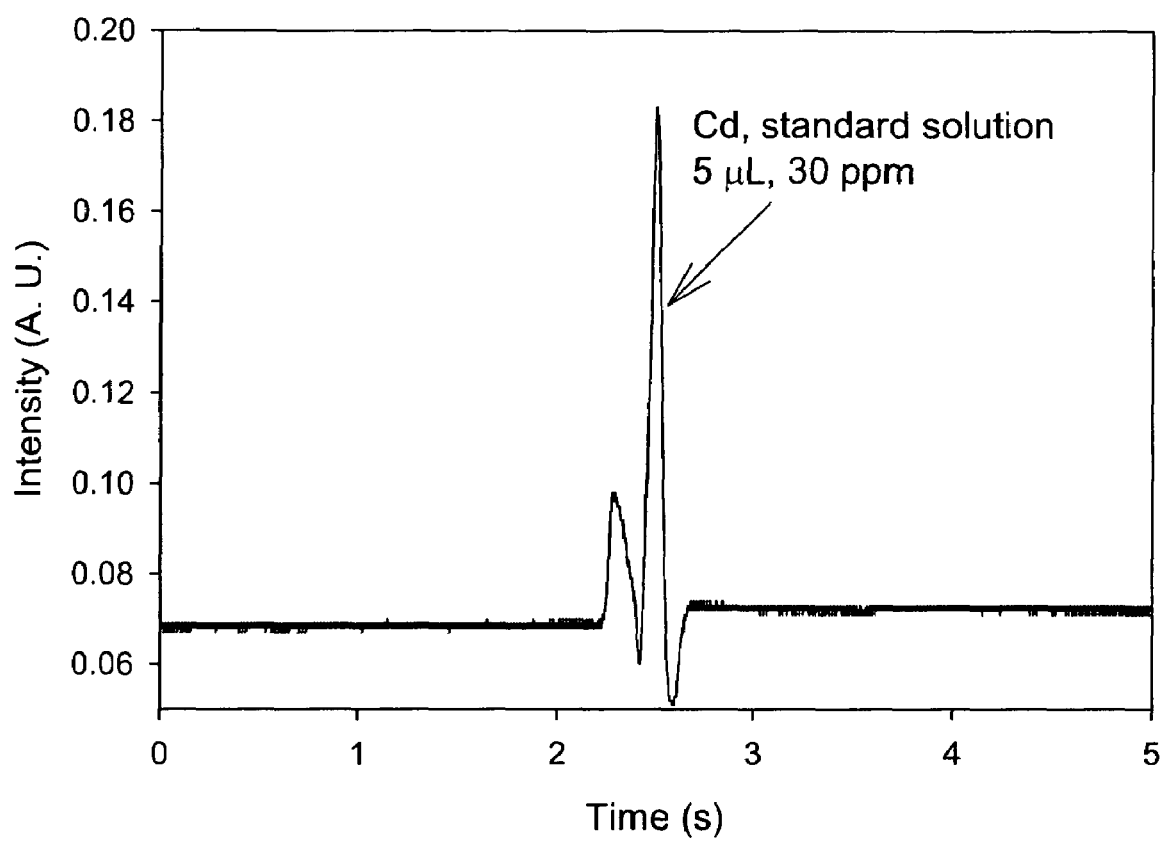
FIG. 29 is a graph of a transient emission signal for Cd obtained from analysis of a 5 µL of a 30 ppm standard solution of Cd with a measurement device having an AC operated, tubular-geometry miniaturized plasma device (of the type shown in FIG. 8 for example) being configured for total ion current measurement using a tubular-geometry device (as shown in FIG. 15 for example)
Figure 30:
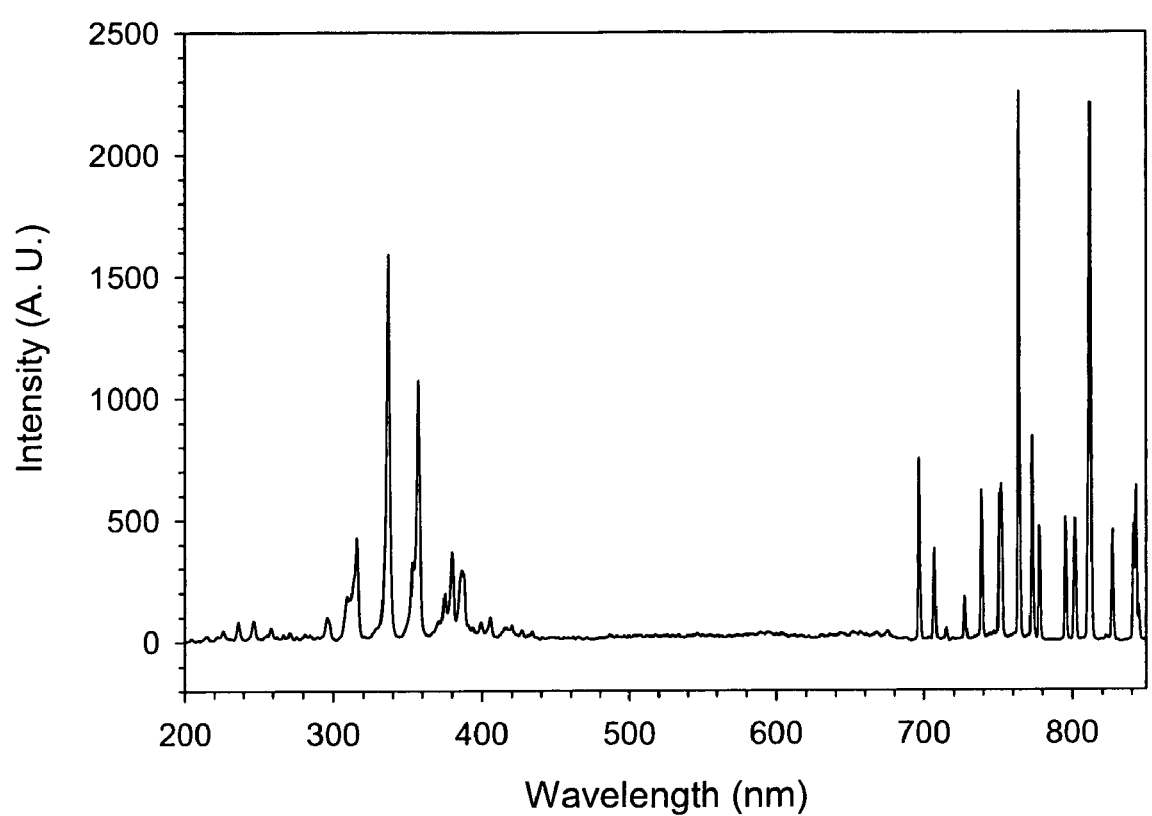
FIG. 30 is a graph of an optical emission background spectrum obtained using a fiber-optic diode-array based spectrometer and the measurement set up shown in FIG. 15; and, FIG. 31 is a graph of a calibration curve obtained by sampling the headspace of a vial containing chloroform, introducing the sample into a miniaturized plasma device (of the type shown in FIG. 8 for example) and by monitoring chlorine emission (at 837.594 nm) using a fiber-optic diode-array based spectrometer and a measurement set up of the type shown in FIG. 15.

Since miniaturized plasma sources have sufficient energy density to ionize analytes introduced into them, can they also be used to provide the total ion current generated from a sample? This was tested by coupling a miniaturized sample introduction system-miniature plasma source combination with a portable, battery-operated atmospheric total ion current detector. An embodiment of the set up used is shown in FIG. 15 and the results obtained are shown in FIG. 29. From the results shown in FIG. 29 it can be concluded that it can. Can complimentary information about a sample (and potentially species quantitation and identification) be obtained by making simultaneous total ion current detection measurements and optical measurements (using, for instance, a portable, battery-operated fiber-optically coupled spectrometer)? This question was addressed using the measurement set up shown in FIG. 15 and by employing the fiber-optically 1511 coupled portable spectrometer 1512 (commercially available from StellarNet inc). From the results shown in FIG. 30 it can be concluded that it can. Clearly, a portable, battery-operated, atmospheric pressure, miniaturized plasma device coupled with portable, battery-operated atmospheric pressure total ion current detector, a portable, battery-operated fiber optically-coupled optical spectrometer and a battery-operated miniaturized ITV sample introduction enable environmental monitoring in the field (e.g., on-site), for example, for monitoring of water samples.

Figure 31:
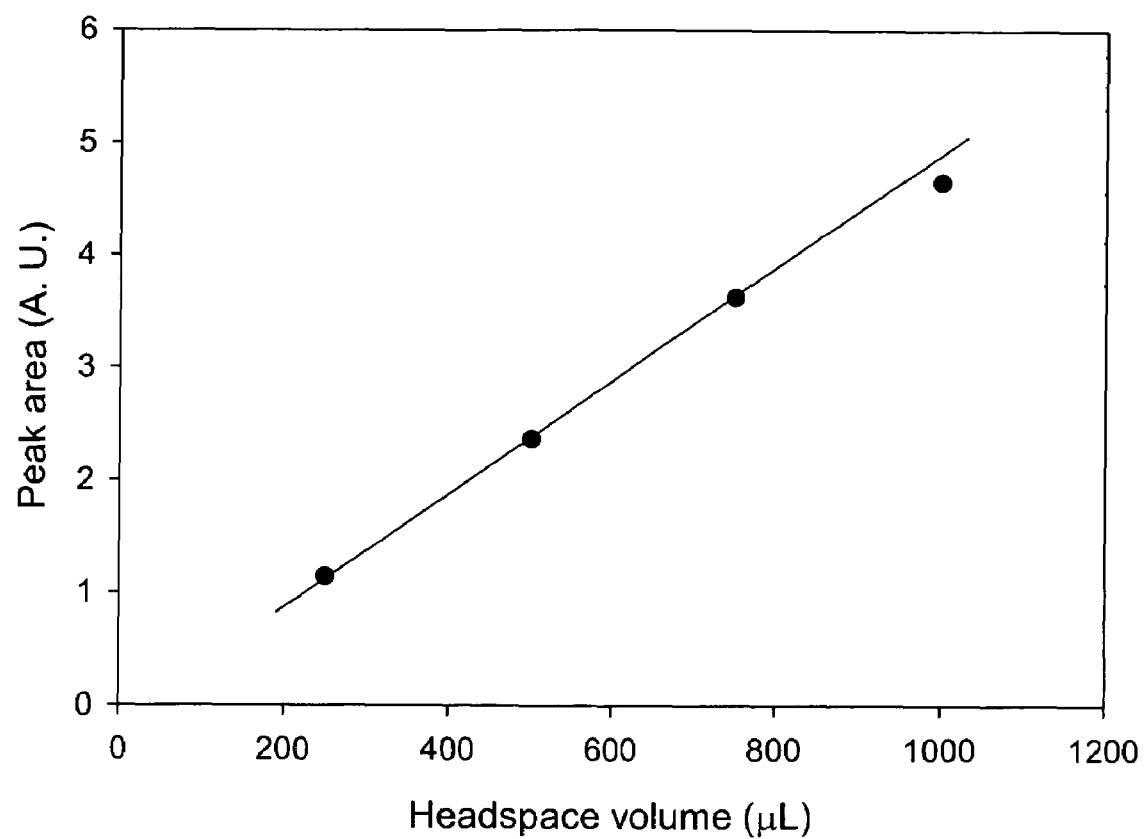

Can miniaturized plasma devices be used with samples that are gases? This was confirmed by sampling (with the aid of a microsyringe) the headspace of a vial containing chloroform and by introducing the gaseous sample in the microsyringe into a miniaturized plasma source device of the type shown in FIG. 8 by piercing a septum (rather than a miniaturized ITV). The septum method of sample introduction has been described in the literature, in V. Karanassios and J. T. Sharples, "Micro-channels and Micro-cells for Gaseous Micro-samples", Sensors and Materials, 9, 363-378 (1997). An example calibration curve is shown in FIG. 31 from which it can be concluded that the miniaturized plasma source devices of the invention can excite halogens introduced into them. Accordingly, these miniaturized plasma source devices may find applicability as embedded detectors in other analytical instruments, such as gas chromatographs (GCs). Those skilled in the art will understand how to interface the capillary column of a GC to the miniaturized plasma source device.

The versatility and utility of the miniaturized plasma source devices of the invention have been demonstrated using gaseous, liquid and solid micro-samples. Unlike ICP sources that can only operate using Ar gas (and sometimes He following modification of the matching network of the plasma power supply), the miniaturized plasma source devices can be sustained using a variety of gases such as Ar, Ar—$H_2$ (3% in $H_2$), He, He—$H_2$, $N_2$ and air, with no modifications required. Due to the low flow-rates used, plasmas could be sustained in the microplasma source devices of the invention even in gases such as Ne, Kr or Xe. Considering the 8-hour operation cost of these microplasma source devices, the cost of even the most expensive of these cases was the same as that of running an ICP source at an aggregate flow-rate of 20 L/min. Furthermore, using such gases, the spectrochemical properties (e.g. electron temperatures, electron concentration, heat capacity, thermal conductivity, spectral line sensitivity etc.) of the miniaturized plasma source devices can be tailored to the analytical problem under consideration, thus enhancing the versatility, capability and analytical utility of these microplasma source devices. In contrast, use of such gases by ICP source is prohibitive due to the costs involved because of the high flow-rates used.

In each of the microplasma source device embodiments, a DC power supply may provide an input voltage of 1-20 V. The DC voltage can then be converted to an AC high voltage (using commercially available power supplies operating at a frequency range between 20-70 kHz). For instance, the AC power supply may operate at a frequency of 35 kHz. Furthermore, for each of the embodiments in which a microplasma source device is connected to a mass spectrometer, a variety of mass spectrometers may be used including quadrupole, ion trap, time-of-flight and magnetic sector mass spectrometers. A portable mass spectrometer is preferable.

The invention is not to be limited by the examples shown herein. According to the invention, the miniaturized plasma source devices can be developed to have different geometries and can be made or microfabricated in various sizes to suit either specific requirements or specific applications. The miniaturized devices can be fabricated using technology that is compatible, for instance, with MEMS fabrication technology or printed circuit or microelectronics techniques. All of these techniques, as well as similar techniques, are within the spirit of the invention. In addition, miniaturized, battery-operated sample introduction devices, as discussed herein, may be used to develop a portable analysis device for elemental analysis of liquid or solid micro-samples. However, for chemical analysis in a laboratory, larger-sized systems that generate dry vapors can be used with the microplasma source devices of the invention. For instance, laser ablation, particle sample introduction, cold vapor generation methods (for determination of hydride forming elements such as As and Se), micro-nebulizers coupled with solvent drying (or desolvating tubes such as commercially available Nafion tubes) or other sample introduction systems that generate dry vapors (e.g. electrothermal vaporization) and even gas phase separations systems (e.g., gas chromatographs) may be used in conjunction with the microplasma source device. Furthermore, the dry sample introduction approaches mentioned above (albeit at a reduced sensitivity for some of them versus miniaturized ITV) can be hyphenated (i.e., used in combination with) miniaturized plasma devices. Such hyphenated approaches include (but are not limited to) flow injection-micronebulizer (with desolvation)-miniaturized plasma device, capillary electrophoresis- micronebulizer (with desolvation)-miniaturized plasma device, and nano-high performance liquid chromatography (nano-HPLC)-miniaturized plasma device, for detection by optical or mass spectrometry. These devices would provide significant advantages in terms of operating costs savings for laboratory devices. For instance, use with a laboratory-scale laser ablation system is possible. A laser ablation system can be interfaced by simply running a tube between the laser ablation cell and the microplasma device. So, instead of connecting the tube from, for instance, a mini-ITV the tube (and as a consequence the sample) bringing the sample comes from a laser ablation cell. If any modifications are required, these would be minor and obvious to those skilled in the art. Cold vapor methods-mentioned after laser ablation offer another example as well as micro-nebulizers with nafion drying tubes. Such sample introduction approaches are also within the scope of this invention.

Exemplary embodiments have been shown which include a mini-ITV or a micro-ITV device integrated with a microplasma device. Further, an atmospheric pressure total ion current detector can be used with the miniature devices to facilitate use in the field. However, the microplasma source devices of the invention may also be connected with large-scale analysis devices as well as large-scale sample introduction devices provided that operating conditions are compatible. In fact, microplasma devices, in accordance with the invention, have been connected with large size mass spectrometers and have provided data that proves that there are sufficient quantity of ions are generated by the microplasma devices of the invention. Also, these devices may find significant applicability with large scale mass spectrometers due to savings in cost per analysis.

In addition, the microplasma source devices of the invention can handle all three sample types; namely, liquids, gases or solids. No conventional source devices can accommodate all three sample types. It should also be known that for the tandem microplasma device discussed earlier, there may be similar embodiments in which there are more than one microplasma tube. Further, it should be noted that these microplasma devices can be used both in the field or in the lab. Also, for the planar embodiments, it should be understood that the wafers may generally be considered to be members, and that each embodiment includes a chamber or channel in which the microplasma is generated and that the term microplasma chamber will refer to each of these particular embodiments.

It should be understood that various modifications can be made to the embodiments described and illustrated herein, without departing from the invention, the scope of which is defined in the appended claims.

The invention claimed is:

1. A measurement device for analyzing a sample, the measurement device comprising:
   a) a sample introduction device configured to receive the sample, vaporize the sample to create a vaporized sample, and deliver the vaporized sample for combination with a microplasma, wherein the sample is one of a liquid, a solid, or a slurry;
   b) a miniaturized microplasma source device connected to the sample introduction device for receiving the vaporized sample from the sample introduction device, generating the microplasma, and combining the microplasma with the vaporized sample to generate one of sample analyte ions or sample analyte photons from the vaporized sample, the microplasma source device comprising:
      i) a microplasma chamber for receiving the vaporized sample;
      ii) a first wafer and a second wafer opposed to the first wafer;
      iii) microchannels located on the surface of at least one of the wafers for forming an inlet conduit, an outlet conduit and the microplasma chamber, with the inlet conduit and outlet conduit being disposed on either side of the microplasma chamber at an angle thereto;
      iv) entrance and exit tubes connected to the inlet and outlet conduits respectively;
      v) a first electrode and a second electrode opposed to the first electrode, the first and second electrodes disposed on opposite sides of the microplasma chamber; and
      vi) a power supply connected to the first and second opposing electrodes, wherein, in use, the power supply applies a voltage to the first and second opposed electrodes for generating the sample analyte ions or the sample analyte photons from the vaporized sample; and
   c) an analysis device connected to the miniaturized microplasma source device for receiving the microplasma and analyzing the microplasma by measuring the one of the sample analyte photons or the sample analyte ions generated by the microplasma.

2. The measurement device of claim 1, wherein the analysis device includes one of a quadrupole, ion trap, time-of-flight, a magnetic sector mass spectrometer and an optical spectrometer.

3. The measurement device of claim 1, wherein the sample introduction device is one of an ITV, mini-ITV, and micro-ITV.

4. The measurement device of claim 1, wherein the microplasma source device is a tandem microplasma source device having two microplasma chambers.

5. The microplasma plasma device of claim 1, wherein the analysis device includes a mass spectrometer and an optical spectrometer for simultaneously measuring emission of the sample analyte photons.

6. The measurement device of claim 1, wherein the electrodes are disposed substantially coplanar with the microplasma chamber and the electrodes include a large portion for connection to the power supply and an inwardly disposed smaller portion being substantially collinear with the microplasma chamber.

7. The measurement device of claim 1, wherein the miniaturized plasma device further comprises:
   a first side wall and a second side wall opposed to the first side wall, the first and second side walls disposed between the first and second wafers, the microplasma chamber being formed between the first and second wafers and the first and second opposed side walls with a first end portion of the microplasma chamber serving as an inlet conduit and a second end portion of the microplasma chamber serving as an outlet conduit, wherein, the electrodes are disposed on opposing facing surfaces of the first and second wafers, and each electrode includes a longitudinally extending portion for connection to the power supply and an inwardly transversely disposed portion wherein the inwardly disposed transverse portions of the electrodes substantially overlap one another in the region of the microplasma chamber.

8. The measurement device of claim 1, wherein the power supply is battery-operated and configured to provide a voltage input of up to 10,000 volts.

9. The measurement device of claim 1, wherein the power supply is an AC power supply operating in the frequency range of 1-300 kHz.

10. The measurement device of claim 1, wherein the sample introduction device is a miniaturized sample introduction comprising:
   a) a sample holder comprising:
      i) a support;
      ii) a coiled-filament disposed on the support for receiving the liquid, slurry or solid samples; and,
      iii) electrical wires running along the support and connected to the coiled-filament,
   b) a vaporization chamber comprising:
      i) an aperture for receiving the sample holder;
      ii) a single inlet aperture for receiving a carrier gas; and,
      iii) a single outlet for venting the sample vapor,
   c) a seal for sealing the vaporization chamber after the sample holder has been placed in the vaporization chamber; and,
   d) a battery-operated power supply connected to the coiled-filament via the wires for applying power to the coiled-filament to dry and vaporize the liquid, slurry or solid samples deposited on the coiled-filament thus producing the sample vapor.

11. The measurement device of claim 1, wherein the sample introduction device is configured to vaporize the sample by electrically heating a coil on which the sample is deposited, and to deliver the vaporized sample to the microplasma using a carrier gas.

12. The measurement device of claim 11, wherein the microplasma source device comprises a power supply configured to operate at in a frequency range of about 1-300 kHz.

13. The measurement device of claim 12, wherein a residence time of the vaporized sample in the microplasma source is at least about 5 seconds.

14. The measurement device of claim 1, wherein the microplasma source device is operated at atmospheric pressure.

15. The measurement device of claim 1, wherein the sample introduction device is one of a cold vapor generation device, a micro-nebulizer coupled with a sulfonated tetrafluorethylene copolymer desolvating tube, an electrothermal vaporization device, laser ablation, particle sample introduction and spark ablation.

* * * * *